(12) United States Patent
Heilman et al.

(10) Patent No.: US 7,588,530 B2
(45) Date of Patent: Sep. 15, 2009

(54) DEVICES, SYSTEMS AND METHODS FOR ASSISTING BLOOD FLOW

(76) Inventors: Marlin Stephen Heilman, 187 Iron Bridge Rd., Sarver, PA (US) 16055; Douglas J. Koebler, 412 Old Rt. 30, Irwin, PA (US) 15642; Daniel R. Moore, 3509 Woodlake Dr., Allison Park, PA (US) 15101; Edward K. Prem, 4027 Gwynedd Dr., Allison Park, PA (US) 15101

( * ) Notice: Subject to any disclaimer, the term of this patent is extended or adjusted under 35 U.S.C. 154(b) by 529 days.

(21) Appl. No.: 11/184,231

(22) Filed: Jul. 19, 2005

(65) Prior Publication Data

US 2006/0014999 A1    Jan. 19, 2006

Related U.S. Application Data

(60) Provisional application No. 60/589,044, filed on Jul. 19, 2004.

(51) Int. Cl.
*A61M 1/10* (2006.01)

(52) U.S. Cl. ............... 600/16; 600/17; 604/4.01; 604/6.11; 623/3.1; 623/3.11

(58) Field of Classification Search ............ 604/4.01, 604/6.11; 600/16, 17; 623/3.1, 3.11
See application file for complete search history.

(56) References Cited

U.S. PATENT DOCUMENTS

| | | | |
|---|---|---|---|
| 3,136,257 A | 6/1964 | Smith | |
| 3,553,736 A | 1/1971 | Kantrowitz | |
| 3,692,018 A | 9/1972 | Goetz | |
| 3,842,440 A | 10/1974 | Karlson | |
| 4,034,742 A | 7/1977 | Thomas | |
| 4,051,840 A | 10/1977 | Kantrowitz | |
| 4,195,623 A | 4/1980 | Zeff | |
| 4,210,409 A | 7/1980 | Child | |

(Continued)

FOREIGN PATENT DOCUMENTS

EP    1 338 294 A2    8/2003

(Continued)

OTHER PUBLICATIONS

Nitta, S. et al., "The Newly Designed Univalved Artificial Heart", ASAIO Transactions, vol. 37, No. 3, M240-M241, Jul.-Sep. 1991.

*Primary Examiner*—Carl H Layno
*Assistant Examiner*—Deborah Malamud
(74) *Attorney, Agent, or Firm*—Bartony & Hare, LLP

(57) ABSTRACT

A pump includes a flexible conduit, at least one valve attached to the flexible conduit about the perimeter of the valve; and a drive mechanism to move the valve to pump blood within the conduit. The drive mechanism can, for example, be adapted to complete a single stroke during each heart ventricle contraction and/or to complete multiple strokes (that is, oscillate) during a single contraction. The moveable valve includes a plurality of openings. Each of the plurality of openings has a closure mechanism in operative connection therewith which is operable to at least partially close the opening to which it is operatively connected when the moveable valve is moved forward and to open the opening to which it is operatively connected when the valve is moved rearward. In one embodiment, each closure mechanism includes a flap of resilient material.

26 Claims, 15 Drawing Sheets

U.S. PATENT DOCUMENTS

| | | |
|---|---|---|
| 4,245,622 A | 1/1981 | Hutchins, IV |
| 4,334,180 A | 6/1982 | Bramm |
| 4,618,789 A | 10/1986 | Flisikowski |
| 4,733,652 A | 3/1988 | Kantrowitz |
| 4,925,377 A | 5/1990 | Inacio |
| 5,108,426 A | 4/1992 | Biro |
| 5,147,281 A | 9/1992 | Thornton |
| 5,266,012 A | 11/1993 | Hashimoto |
| 5,676,162 A | 10/1997 | Larson, Jr. |
| 5,676,651 A | 10/1997 | Larson, Jr. |
| 5,722,930 A | 3/1998 | Larson, Jr. |
| 6,375,607 B1 | 4/2002 | Prem |
| 2004/0097782 A1 | 5/2004 | Korakianitis |

FOREIGN PATENT DOCUMENTS

| | | |
|---|---|---|
| WO | WO 2006/020273 A2 | 2/2006 |

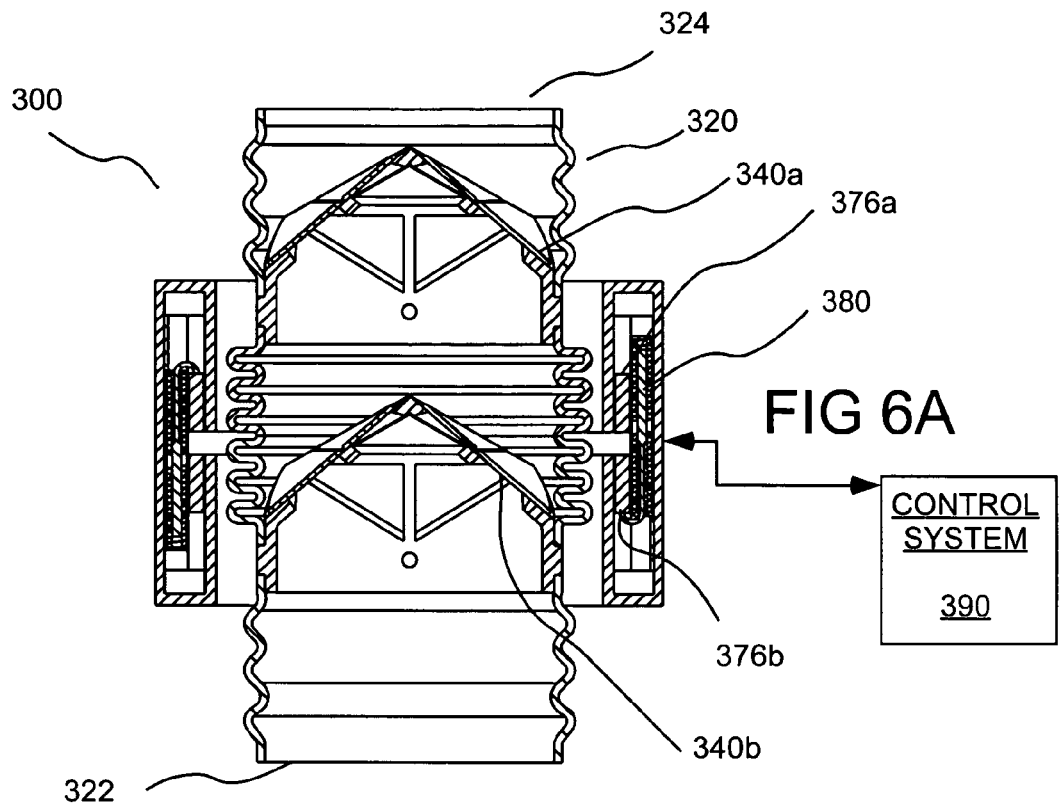
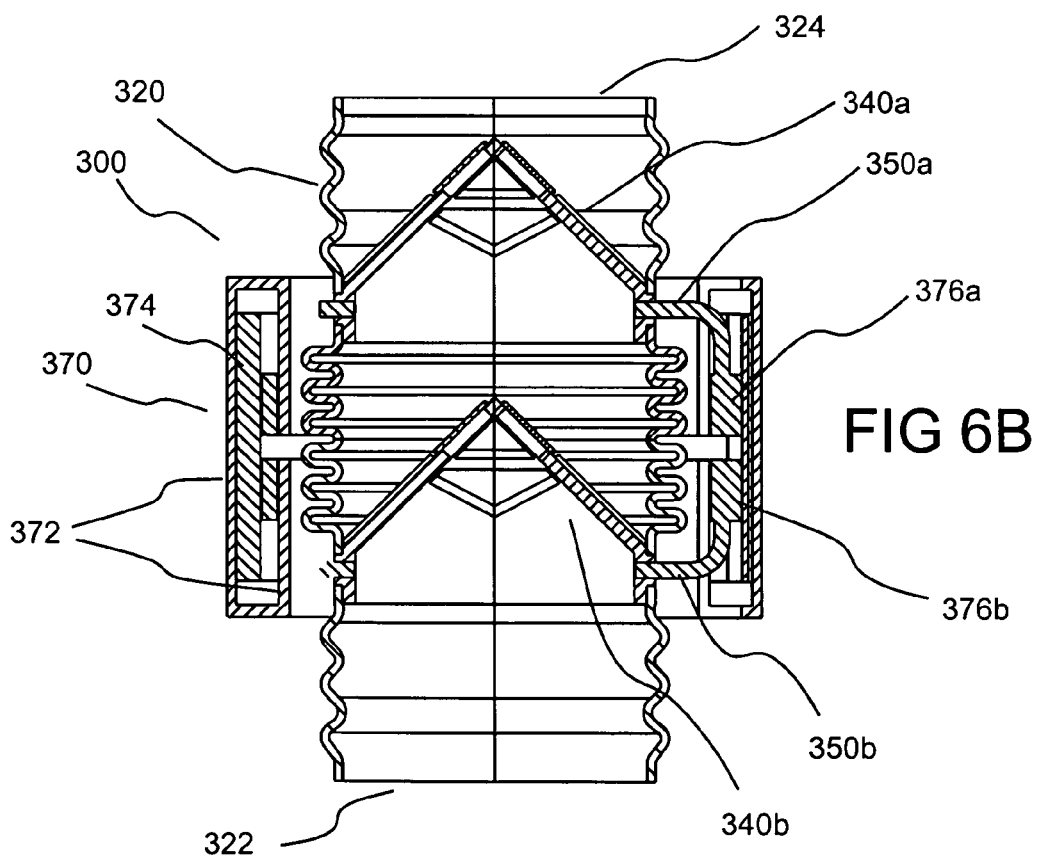

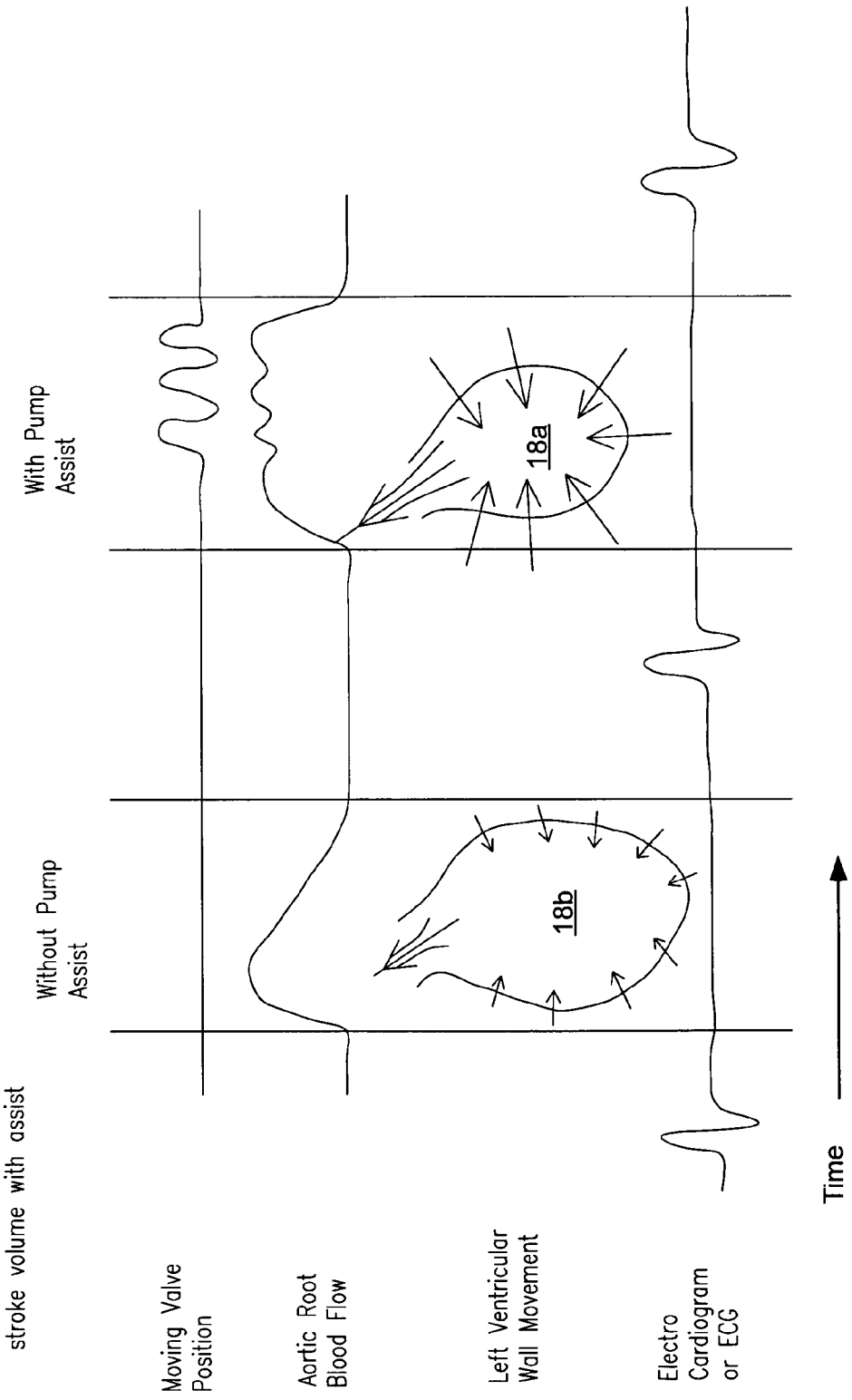

DEVICES, SYSTEMS AND METHODS FOR ASSISTING BLOOD FLOW

CROSS-REFERENCE TO RELATED APPLICATION

This application claims benefit of U.S. Provisional Patent Application No. 60/589,044, filed Jul. 19, 2004, the disclosure of which is incorporated herein by reference,

BACKGROUND OF THE INVENTION

The present invention relates generally to devices, systems and methods for assisting blood flow, and, particularly, to blood pumps that include a moving (for example, an oscillating) valve assembly to propel blood. The pumps of the present invention can be either fully implanted or temporarily connected to the circulation using percutaneous blood conduits. The pumps of the present invention can, for example, be fully or completely implanted for months to years to alleviate or correct heart failure and related symptoms.

Heart failure, or the inability of the heart to pump sufficient blood for the body's needs, results in very poor quality of life, huge costs to society, and hundreds of thousands of yearly deaths. Heart failure is caused by an abnormally low cardiac output. Cardiac output is the out flow of blood from the heart and is measured in liters of blood flow per minute or l/min. Cardiac output for a normal man at rest or during light activity is around 5 liters per minute. Severe heart failure exists when the cardiac output is as low as 2.5 to 3.5 liters per minute. For an average man in heart failure with a heart rate of 80 beats per minute, the average amount of blood that is pumped with each heartbeat or stroke volume might be 37 milliliters or ml. The same man with a normal heart might pump 62 milliliters with each heartbeat. An ideal treatment for heart failure would boost the low 37 ml stroke volume up to the normal 62 ml stroke volume.

The main pumping chamber of the heart or left ventricle, LV has an inlet mitral valve and an outlet aortic valve. During left ventricular contraction or systole, the inlet valve closes as blood is pushed through the aortic valve into the aorta or main artery to the body. When the LV is resting during diastole, LV pressure may be between 2 and 20 mm of Hg pressure. This diastolic pressure is termed the LV preload and the preload will be in the higher end of its pressure range during heart failure. During active LV contraction or systole, the LV must eject its blood against the pressure in the aorta. Aortic pressure is typically between 70 and 140 mm Hg Pressure. This aortic pressure is termed the after-load. It is well known that, if the after-load is reduced in heart failure, the LV stroke volume will naturally increase and this increase is one reason that afterload-reducing drugs such as ACE-inhibitors help heart failure patients.

Blood pumps which lower the aortic pressure after-load are attractive because they allow the failing LV to eject more blood with less effort. However, no after-load reducing devices have thus far been shown to be practical for indefinitely supporting the failing LV. Instead, all long term (that is, months to years), commercially available heart assist devices, whether rotary turbine pumps or collapsing chamber pumps go around or bypass the failing LV, pumping blood from the LV apex through the pump into the aorta. By doing so, they act in parallel to the LV and essentially compete with the LV in their pumping action. This pumping competition has several negative complications including right heart failure, fusion of the aortic valve over time and the risk of collapsing the LV. Collapsing chamber pumps are physically large and cannot be implanted in some small patient because of their size. Rotary turbine pumps are attractively small, but have other limiting complications. For example, the rotary turbine pumps induce high levels of shear stress in the blood elements and also may reduce the normal pulsatility of the blood entering the aorta. The effect of the high shear stress on the blood cells is to promote blood clotting which can lead to strokes and heart attacks. Physicians try to reduce this blood clotting by giving the patients anticoagulants and this, in turn, puts the patients at risk of excessive bleeding. These clotting and bleeding complications are substantial limitations to broader use of rotary turbine assist pumps.

For short-term heart assist (that is, hours to days), a common method of providing cardiac assist is the use of counter-pulsation devices such as intraaortic balloon pumps or IABPs. IABPs provide an afterload-reducing type of assist. As described in U.S. Pat. Nos. 4,733,652 and 3,692,018 by Kantrowitz et al. and Goetz et al., the main benefit of such devices stems from after-load reduction of the left ventricle during systole and providing increased diastolic pressure for perfusing the coronary and other arteries during diastole. Typical patients needing this type of treatment suffer from cardiogenic shock or need perioperative circulatory support. The nature of IABP design restricts itself to acute use only, since the bulky balloon drive mechanism remains outside the patient's body necessitating patient confinement to a hospital bed.

A "dynamic aortic patch" is disclosed in U.S. Pat. No. 4,051,840, to Kantrowitz et al. and is in clinical trials. It is surgically and permanently attached to the patients descending aorta and is pneumatically activated by an external air pump. Such a pump lowers the LV after-load, facilitating left ventricular contraction and increasing stroke volume.

Pouch-type auxiliary ventricles attached to the patient's aorta have been described. These devices use mechanical or pneumatic means for the pumping the blood contained in the pouch and are disclosed in U.S. Pat. Nos. 3,553,736 and 4,034,742 by Kantrowitz et. al. and Thoma. Some of these devices have a single access port to the aorta that serves as both the inlet and the outlet for blood flow. Single port designs have the disadvantage of recirculation and relative flow stagnation, increasing the risk of clot formation and thromboembolism. Others have both inlet and outlet ports to the aorta and are typically connected in parallel with the aorta. See, for example, U.S. Pat. Nos. 4,195,623 and 4,245,622 by Zeff et al. and Hutchins et al.

U.S. Pat. Nos. 5,676,162, 5,676,651, and 5,722,930, by Larson et al., describe a single stroke moving valve pump designed for ascending aortic placement. The Larson device uses a commercially available artificial heart valve with attached magnets and requires excision of a portion of the aorta. A series of separate electric coils step the valve/magnet combination forward in a sliding action within a cylinder. The device is quite large for the limited space available between the heart and the take-off vessels from the aorta to the upper body and brain. The device is designed to have one stroke in synchronization with each LV systole. The blood volume required for closing commercially available heart valves is typically 2-5 ml and therefore multiple smaller oscillations per heart contraction would suffer from volumetric inefficiency. Another problem with the Larson device is the tight crevice between the cylinder wall and the moving valve. This tight space results in high blood shear and the resultant risk of blood clotting complications. The same problem exists with a moving valve pump described by Child, U.S. Pat. No. 4,210, 409. The Child pump has two valves, one stationary and one moving.

Thornton, U.S. Pat. No. 5,147,281 discloses an oscillatory valve blood pump that is external to the body and fits in an enclosure the size of a briefcase. It uses a stationary coil to attract a magnetic tube encasing a one-way valve. Its forward stroke propels blood until the tube assembly stops and is repelled backward by return leaf springs that were charged during the forward stroke. A second stationary valve is sometimes in the circuit. A stretchable silicone rubber tube connects the tube or pipe-valve assembly with the pumps inlet and outlet.

Nitta, in ASAIO Transactions 1991:37: M240-M241 describes a "univalved artificial heart" powered electro-magnetically wherein the valve oscillates within the frequency range of 1 to 30 Hz. The valve is contained in a tube, with attached magnetic material. Stationary electric coils actuate the tube-magnet-valve combination. The valve is described as a jellyfish valve. One problem with jellyfish valves is the compound curvature or wrinkling of the membrane that occurs when the valve opens and closes. One can liken the action of the jellyfish valve to that of an umbrella that oscillates between a circular flat membrane and a wrinkled umbrella shape as it closes and opens. Wrinkling of the membrane is virtually impossible to prevent in a jellyfish valve and introduces stresses and strains that significantly limit the life of the valve.

Hashimoto, U.S. Pat. No. 5,266,012, also uses a jellyfish valve in a vibrating pipe blood pump intended for use outside the body. The purpose of this invention is to make the vibrating tube pump portion separable from the drive mechanism so that the blood-contacting portion of the pump can be disposable.

Although numerous pharmacologic, biologic, and mechanical interventions have been devised to address heart disease/failure (some of which are described above), heart failure remains a major public health problem with an estimated five million victims in the United States alone. It is, therefore, very desirable to develop improved devices, systems and methods of assisting the heart in pumping blood through the circulatory system.

SUMMARY OF THE INVENTION

In one aspect, the present invention provides pump, which can, for example, be partially or fully implantable within a patient, for assisting blood flow. The pump includes a flexible conduit, at least one valve attached to the flexible conduit about the perimeter of the valve; and a drive mechanism to move the valve to pump blood within the conduit. The drive mechanism can, for example, be adapted to complete a single stroke during each heart ventricle contraction and/or to complete multiple strokes (that is, oscillate) during a single contraction.

The flexible conduit can be generally linear or can be arced. When the conduit is arced, the drive mechanism is preferably adapted to move (for example, oscillate) the valve on an arced path. The valve can, for example, be in operative connection with a pivot arm which is in operative connection with the drive mechanism.

A wide variety of drive mechanisms can be used in the pumps of the present invention. For example, the drive mechanism can include a brushless direct current electric motor. The drive mechanism can further include a speed reduction mechanism in operative connection with/between the brushless direct current motor and the valve. In one embodiment, the speed reduction mechanism includes a gear system (for example, one or more sets of planetary gears in operative connection with a sun gear).

In another embodiment, the drive mechanism includes an electromagnetic motor including at least one magnetically conductive plate. The magnetically conductive plate can be curved to effect movement of the valve in an arcuate path. The electromagnetic motor can further include at least one moveable coil. The at least one moveable coil can, for example, include aluminum wiring.

In another embodiment, the drive mechanism includes at least one hydraulic pump.

The pump preferably further includes a control mechanism in operative connection with the drive mechanism. The control mechanism can, for example, be adapted to actuate the drive mechanism during systole and, preferably, in the later half of systole.

In one embodiment, the valve includes a plurality of openings or valve ports (which can be formed separately in a valve frame). Each of the plurality of openings has a closure mechanism (or valve) in operative connection therewith. Each closure mechanism is operable to at least partially close (preferably substantially or completely close) the opening to which it is operatively connected when the moveable valve is moved forward and to open the opening to which it is operatively connected when the valve is moved rearward. Each of the closure mechanisms can, for example, include a flap of resilient material. In this embodiment, each of the flaps is preferably placed in operative connection with the corresponding opening so that the resilient material of the flap flexes without complex curvature. In one embodiment, each of the openings comprises at least one generally linear side and the flap is attached to the generally linear side. Each of the openings can be angled with respect to the direction of flow, thereby reducing the volume of fluid required to be displaced to close each of the closure mechanisms.

The pump can further include a housing encompassing at least a portion of the flexible conduit. In one embodiment, pressure within the housing outside of the flexible conduit is maintained to be generally the same as pressure within the flexible conduit. For example, a fluid can be contained within the housing outside of the fluid conduit. The pressure of the fluid can be maintained at generally the same pressure as a pressure within the flexible conduit. In general, the volume of the fluid outside the fluid conduit can be chosen so that it equals the volume within the housing outside of the fluid conduit when the fluid conduit is in an unstressed (unpressurized) state.

The pump can further include an inflow conduit in fluid connection with a first, inflow end of the flexible conduit. The inflow conduit is adapted to be placed in fluid connection with a blood vessel. The pump further includes an outflow conduit in operative connection with a second, outflow end of the flexible conduit. The outflow conduit is adapted to be placed in fluid connection with the blood vessel. In one embodiment, the inflow conduit and the outflow conduit are further adapted to place the pump in series connection with the blood vessel via a single cut in the blood vessel without removing a section of the blood vessel. The single cut in the blood vessel can, for example, be a dissecting cut of the blood vessel, creating a first section of the blood vessel remaining in fluid connection with the heart and a second section of the blood vessel which is no longer in fluid connection with the heart. The inflow conduit in this embodiment is adapted to be placed in fluid connection with the first section of the blood vessel, and the outflow conduit is adapted to be placed in fluid connection with the second section of the blood vessel. Each of the inflow conduit and the outflow conduit can, for example, be flexible. The direction of flow or lines of flow in the inflow conduit and outflow conduit can "cross" so that the inlet of the inlet conduit and the outlet of the outlet conduit can be placed in close proximity to each other with respect to the length of the blood vessel (for example, within 0 to 2 cm of each other. The inflow conduit and the outflow conduit can also be in fluid connection with a flow device that is insertable within a single longitudinal cut in the blood vessel.

In another aspect, the present invention provides an implantable pump for assisting blood flow, including: a flexible conduit formed in an arc; at least one valve attached to the conduit about the perimeter of the valve; and a drive mechanism to move the valve in an arced path to pump blood within the conduit.

In a further aspect, the present invention provides an implantable pump for assisting blood flow, including: a flexible conduit; an extending arm; a drive mechanism in operative connection with the extending arm to move the extending arm; and at least one movable valve in operative connection with the extending arm. Movement of the valve is operable to cause flow of blood through the flexible conduit. The extending arm can, for example, move the valve in an arcuate path. In one embodiment, the extending arm pivots about a pivot point. The valve can, for example, be attached to the flexible conduit about the perimeter of the valve.

In a further aspect, the present invention provides a pump including a conduit and at least one moveable valve within the conduit. The moveable valve includes a plurality of openings. Each of the plurality of openings has a closure mechanism in operative connection therewith. Each closure mechanism is operable to at least partially close the opening to which it is operatively connected when the moveable valve is moved forward and to open the opening to which it is operatively connected when the valve is move rearward. The pump further includes a drive mechanism to move the valve to pump blood within the conduit. In one embodiment, each closure mechanism includes a flap of resilient material.

In another aspect, the present invention provides an implantable pump for assisting blood flow, including: a conduit; at least one moveable valve within the conduit; and a drive mechanism to move the at least one valve to pump blood within the conduit. The drive mechanism includes an electromagnetic motor including at least one moveable coil in operative connection with the at least one valve via, for example, an extending member.

In one embodiment, the electromagnetic motor is generally linear and is operative to move the valve along a generally linear path. In another embodiment, the electromagnetic motor is arcuate and is operable to move the valve along a generally arcuate path. In one embodiment, the at least one moveable coil of the electromagnetic motor includes aluminum wiring.

In another aspect, the present invention provides a method of assisting blood flow including the steps of: effecting a single cut in a blood vessel without removing a section of the blood vessel; and connecting an inflow conduit and an outflow conduit of a pump in connection with the blood vessel via the single cut so that the pump is in serial connection with the blood vessel. In one embodiment, the single cut in the blood vessel is a dissecting cut of the blood vessel, creating a first section of the blood vessel remaining in fluid connection with heart and a second section of the blood vessel which is no longer in fluid connection with the heart. In this embodiment, the step of connecting the inflow conduit and the outflow conduit includes the steps of connecting the inlet conduit to the first section of the blood vessel and connecting the outflow conduit to the second section of the blood vessel. In another embodiment, the single cut in the blood vessel is a longitudinal cut and the inflow conduit and the outflow conduit are in fluid connection with a flow device that is inserted within the blood vessel via the longitudinal cut. The blood vessel can, for example, be the aorta or the pulmonary artery. In many cases, the blood vessel is the ascending aorta to assist a failing left ventricle.

In a further aspect, the present invention provides a method of assisting blood flow including the steps of: placing a pumping mechanism in serial connection with a blood vessel (for example, the ascending aorta); and actuating the pumping mechanism only in the second half of systole.

In still a further aspect, the present invention provides an implantable pump for assisting blood flow, including: a flexible conduit; at least one moveable valve to effect blood flow within the conduit; a drive mechanism to move the valve to pump blood within the conduit; and a housing surrounding at least a portion of the flexible conduit. The valve is positioned within the conduit. The housing has a fluid therein which surrounds the flexible conduit and operates to equalize a pressure within the housing outside of the conduit to the pressure within the conduit. The moveable valve can, for example, be attached to the flexible conduit about the perimeter of the valve.

A primary purpose of the devices, systems and methods of the present invention is to allow a heart failure patient to regain a normal cardiac output and therefore a normal life. Heart failure patients typically have a weakened and dilated left ventricle or LV. During LV contraction in heart failure, the heart squeezes out a limited amount of blood and then stalls for a period of time unable to complete its full ejection of blood. During this stall period, the LV maintains pressure near the aortic pressure level but since no blood is being ejected, no useful work is being performed. It is at this time, later in systole that one, two or more strokes of the valve pumps of the present invention described herein can supplement the heart's stroke or ejected volume to reach a normal level. Since the LV pressure is near that of the aorta in the latter half of systole, the assist pump work is considerably less than if the pressure difference was that between the aorta and the LV during its resting time or diastole. This strategic pump timing allows the pump motors of the present invention to be much smaller than they would otherwise have to be.

Another purpose of the invention is to be capable of full implantation and be attachable to, for example, the ascending aorta without interfering with coronary artery bypass grafts that are typically attached to this ascending aortic location. Hundreds of thousands of heart failure patients have such grafts. Preferably, the inflow and outflow conduits of the pumps of the present invention can place the pumps of the present invention in serial connection with the aorta via a single cut to the aorta and without removal of any section of the aorta. To facilitate this objective, in one embodiment the flow conduit of the pump of the present invention is curved approximately 180 degrees or more so that its conduits can be readily attached to the severed ends of a blood vessel such as the aorta without excising any aortic section and its possibly connected coronary artery bypass grafts. The curved nature of the pumps of the present invention distinguishes such pumps from other moving valve pumps, which function in a linear fashion.

It is also preferable to substantially reduce the length of or completely eliminate the linear, rigid pipe or tube section that is an integral part of previously described moving valve pumps. In previously described moving valve pumps known to the inventors, such pipes provide a larger defined volume of blood for building momentum and causing forward flow with the forward stroke of the tube or pipe-valve assembly. Moreover, drive elements such as magnets can be placed on such pipes or tubes. To, for example, provide lighter weight, less vibration, a smaller pump size and better anatomical fit in the patient, several embodiments of the pumps of the present invention eliminate the tube or pipe found in other moving valve pumps and compensate for any smaller blood volume movement with increased valve action. In general, there is little space for a pipe or tube in addition to a suitable length of long-lived stretchable blood conduit in the upper right chest cavity.

BRIEF DESCRIPTION OF THE DRAWINGS

Other aspects of the invention and their advantages will be discerned from the following detailed description when read in connection with the accompanying drawings, in which:

FIG. 6A is a cross-sectional view of another embodiment of a pump of the present invention including two moving valves and a direct electric motor drive mechanism.

FIG. 6B is another cross-section view of the pump of FIG. 6A.

FIG. 11 is a diagram of the interrelationship between the electro-cardio-graphic signal, the patient's contracting left ventricle, the blood flow leaving the left ventricle and the moving valve action of the pump of the present invention.

DETAILED DESCRIPTION OF THE INVENTION

The pumps of the present invention can, for example, assist or augment cardiac output via in-series placement with a blood vessel such as the ascending aorta just above the heart of a patient suffering from heart disease. The pumps of the present invention can, for example, alternatively or additionally be placed in series connection with the pulmonary artery. In several embodiments of the pumps of the present invention, a multi-stroke or oscillating valve is used to induce blood flow. As used herein, the term "multi-stroke" refers to a valve that oscillates (that is, moves forward and rearward) more than once for each left ventricle contraction.

Figure 1:
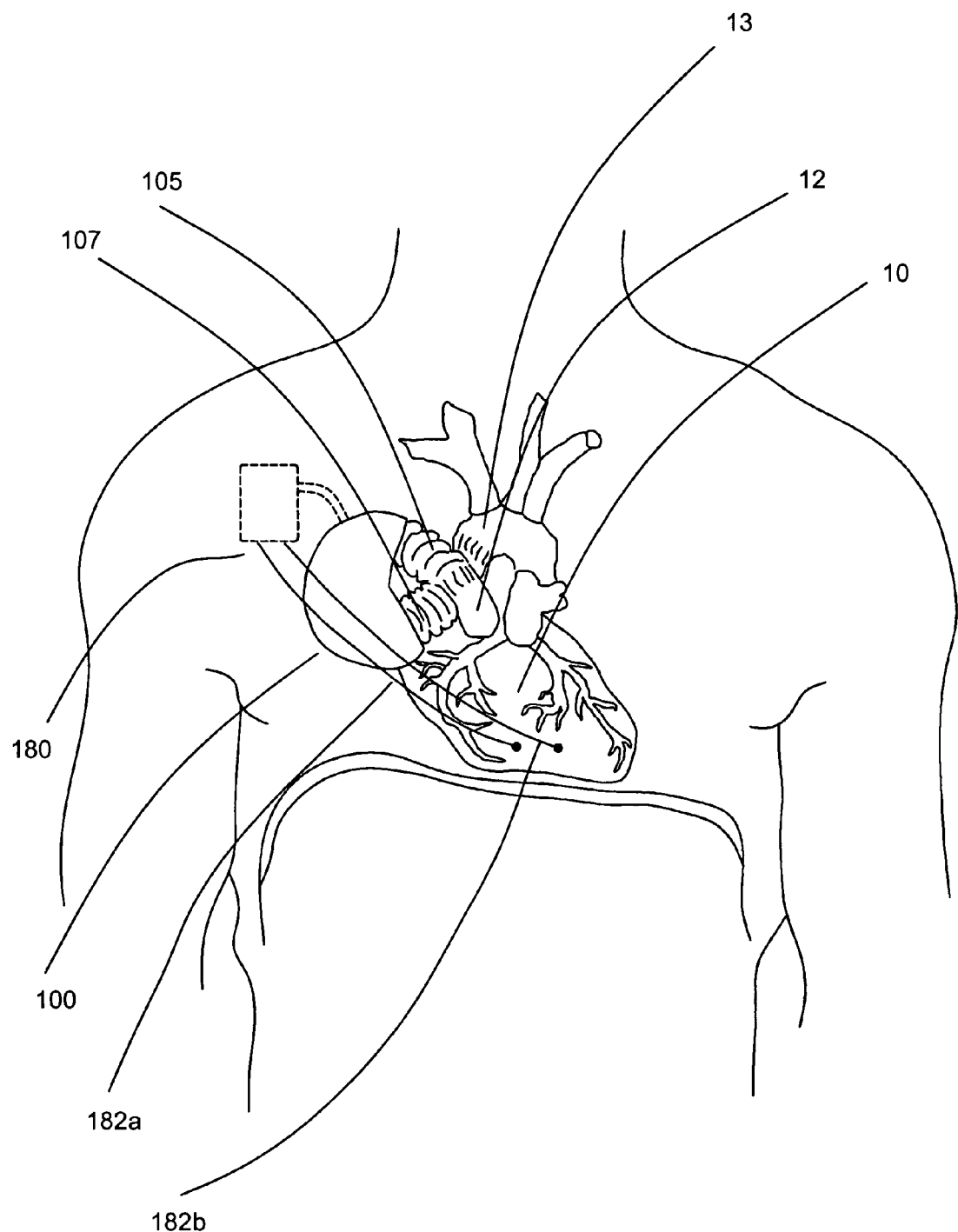
FIG. 1 is a view of one embodiment of a pump of the present invention implanted in a patients upper right chest and connected to the patients ascending aorta by means of two grafts extending from the pump.

Referring now to the drawings, wherein like reference numerals refer to the same item, there is shown in FIG. 1 a pump 100 connected to the ascending aorta at the output of the patients heart 10. In a fully implanted pump configuration as illustrated in FIG. 1, the pump 100 is be placed close to the ascending aorta in the upper right chest cavity. Because there is limited space in the right upper chest, especially in small patients, it is desirable that the size of the pumps of the present invention be small, and that the form factor of the pump be compact. In placement in the upper right chest, the pump will displace a certain volume of the upper right lung. The displaced lung volume is a relatively small penalty to pay, however, because there is relatively little gas diffusion occurring in this upper portion of the lung.

Typically, the weight density of the pump 100 and other pumps of the present invention will exceed the weight density of the lungs. This difference in weight density necessitates connecting the pump to some relatively fixed structure such as the patient's rib cage. The rib cage conveniently surrounds the space in the upper right thorax. Such fixation can, for example, include suturing the pump to one or more ribs for stabilization.

Figure 2:
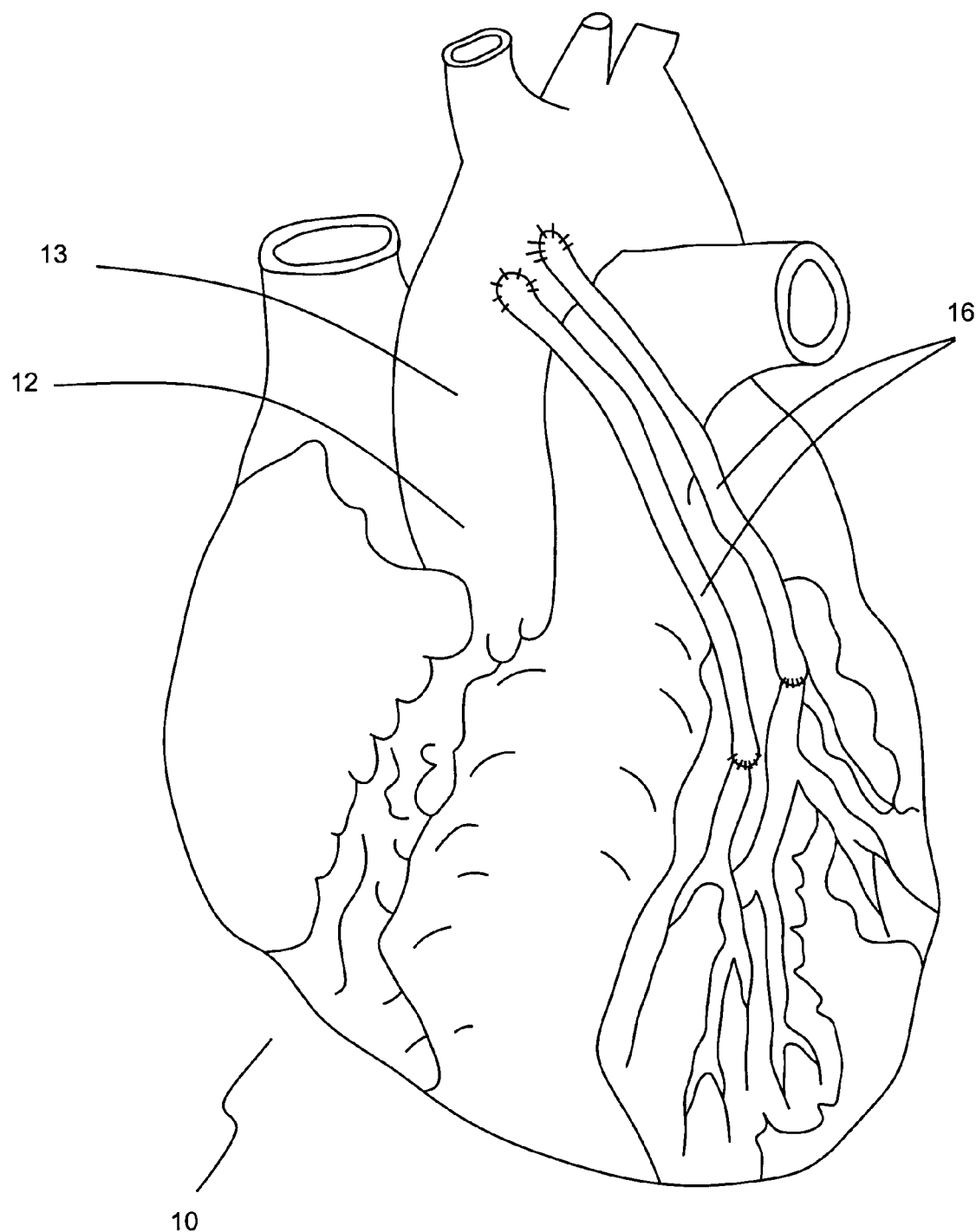
FIG. 2 is a view of a human heart with two coronary artery bypass grafts connected between the ascending aorta and the coronary arteries on the surface of the heart.

In the embodiment of FIG. 1, pump 100 is placed in series connection with the ascending aorta via two flexible connecting conduits such as synthetic grafts 105 and 107, which are, for example, respectively sewn to two severed ends of the ascending aorta. The blood leaving the heart flows through the lower ascending aorta 12 into the inflow graft 105, through the pump 100 and back to the upper ascending aorta 13 by means of the outflow graft 107. It is an important advantage that this pump connection can be made without excising or removing any portion of the aorta. The reason this is important can be seen in FIG. 2, which illustrates vein grafts 16 that are connected from the ascending aorta to the coronary arteries of the heart. Millions of heart patients have had coronary artery bypass surgery and have such vein grafts 16 connected to their ascending aorta. If a portion of the aorta had to be removed, those grafts connected to the removed portion of the aorta would be destroyed or, at the very least, would have to be surgically reconnected. Instead, the pump 100 and its connections are preferably configured such that a continuous blood flow pathway is established without removing a section of the aorta. One way of accomplishing this objective (as illustrated in FIG. 1) is to effect a single cut across or trans-secting the aorta (preferably below any bypass graft connections) and, subsequently, connect the end of the pump's inflow graft 105 to the lower cut end of the ascending aorta. The end of the pumps outflow graft 107 is connected to the upper end of the trans-sected ascending aorta. The pump is thus placed in series with the heart, which avoids the problems associated with establishing a blood flow pathway that is in parallel with the heart.

Under these circumstances, the form of the pump's blood pathway minimizes pump and connection size and provides a good fit to the available anatomy. The blood flow pathway or conduit 120 (as described below) in the pump 100 is, for example, arcuate and has a radius of curvature of greater than 180°. The flow conduit 120 can have a relatively tight radius of curvature (for example, approximately 0.75 to 2 inches). A housing 130 encompasses conduit 120 and is similarly curved or arcuate in shape.

Figure 1A:
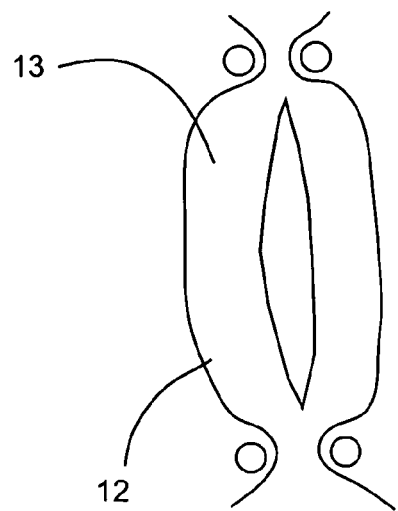
FIG. 1A is a view of the ascending aorta without coronary artery bypass grafts.
Figure 1B:
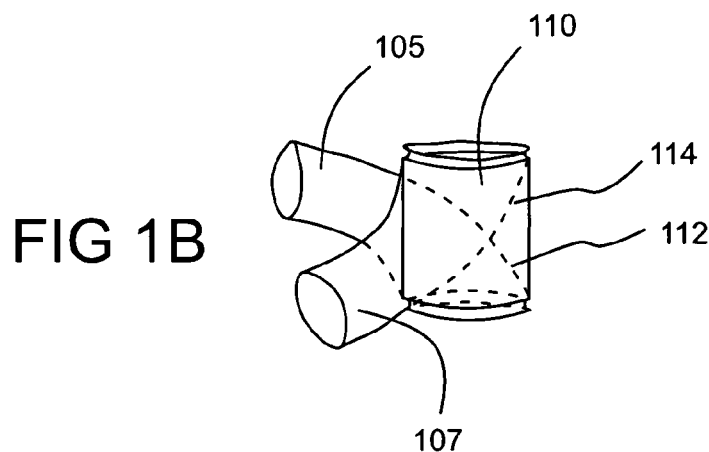
FIG. 1B is a view of one embodiment of a cylindrical, implantable structure or device having integral, crossing blood flow pathways.
Figure 1C:
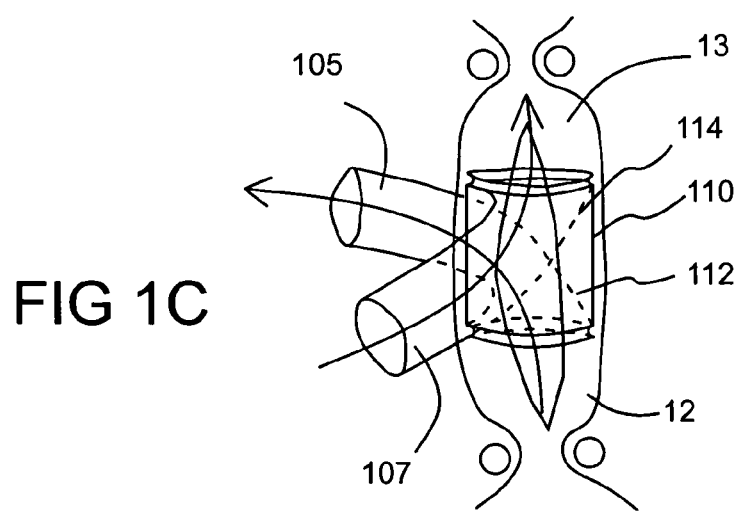
FIG. 1C is a view of the aorta with the cylindrical structure of FIG. 1B inserted therein to establish a serial blood flow connection between the pump and the aorta.

An alternative to the aortic connection discussed above is shown in FIGS. 1A, 1B, and 1C. In this embodiment, a generally cylindrical flow structure or device 110 is dimensioned to fit inside, for example, the ascending aorta and is inserted into the aorta through a single longitudinal incision in the aorta. This connection method can be used in a section of aorta that does not have attached coronary artery grafts. Use of the cylindrical structure 110 does not require the transection of the aorta and can be used for temporary or permanent attachment to the aorta. Traversing the longitudinal incision in the aorta are the inflow and outflow grafts 105 and 107, respectively, coming from the pump 100. Within the cylindrical structure 110 are crossing blood flow pathways 112 and 114. Blood flow passes from the proximal or lower aorta into flow pathway 112 of structure 110 and into inflow graft 105. Blood exits the pump 100 via outflow graft 107 and flows into the distal or upper aorta through flow pathway 114 of the cylindrical structure 110. Preferably, the axial length of flow structure or device 110 is minimized. For example, in certain embodiments, the length of flow structure or device 110 is preferably no more than 3 cm and, more preferably, no more than 2 cm.

Figure 3:
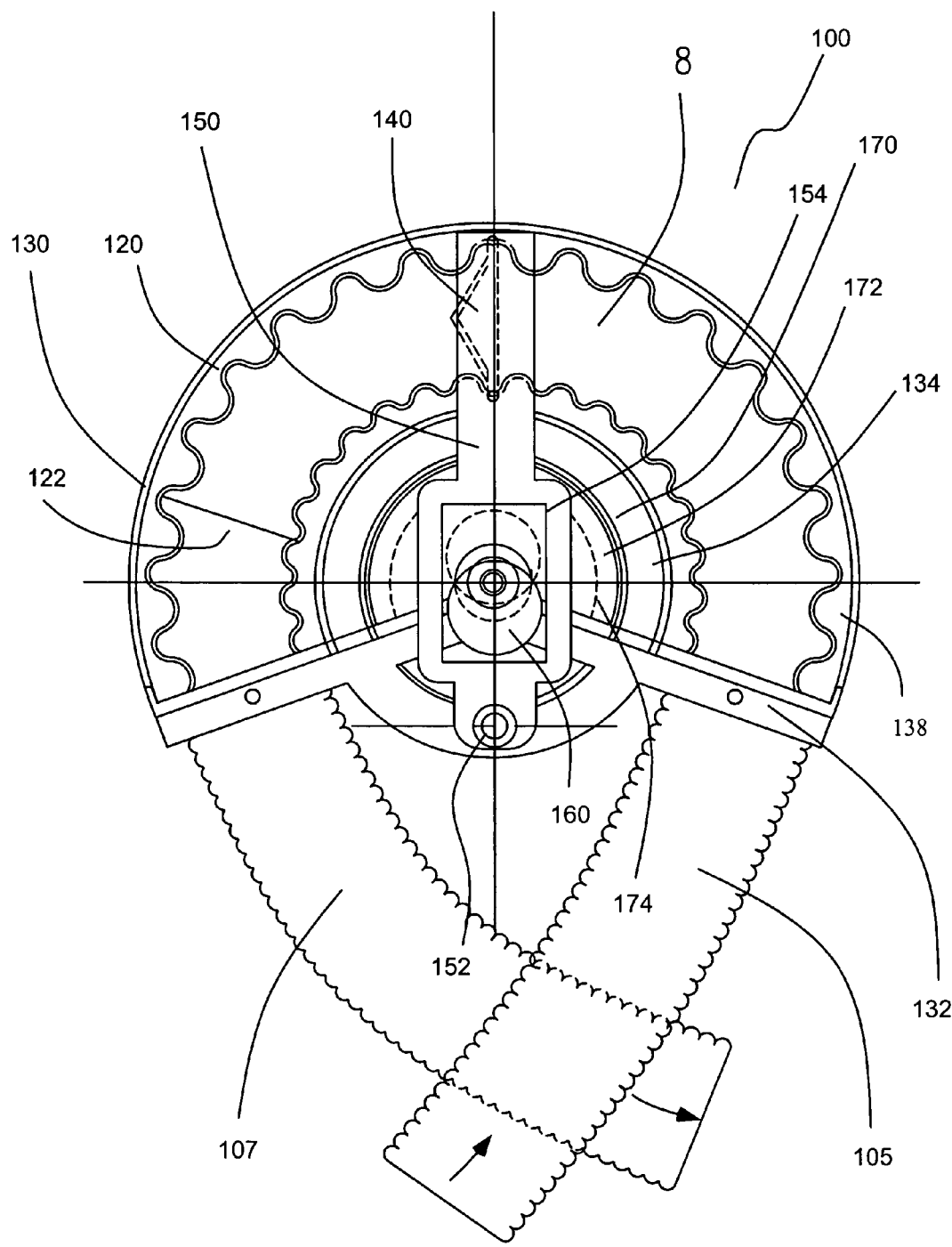
FIG. 3 is a side, transparent view of the pump of FIG. 1 including an electric motor and speed reducing gear mechanism for actuating the pump.

FIG. 3 is a side view of pump 100. In the illustrated embodiment, inflow graft 105 connects seamlessly with a moveable (for example, a stretchable and/or corrugated) blood flow conduit 120 within an opening in a header portion 132 of housing 130. The blood flow pathway through the grafts 105 and 107 and pump 100 is completed by a similar connection of the outflow graft 107 to corrugated blood flow conduit 120 in a second opening within header 132. The grafts 105 and 107 can, for example, be commercially available FDA-approved flexible DACRON® or TEFLON® vascular grafts. The stretchable corrugated blood flow conduit 120 is specially designed and constructed so that it can be extended and compressed along its length as a valve 140 oscillates. Valve 140 is, for example, placed inside the blood conduit 120 approximately midway in the curved length of the conduit 120. In several embodiments, valve 140 is attached (for example, by an adhesive) around the perimeter thereof to blood flow conduit 120. As described above, the walls of the conduit 120 can be corrugated, stretchable or otherwise moveable along the path of movement of valve 140 to allow movement (for example, via contraction and expansion) of the conduit 120 as the valve 140 moves back and forth. In the case that conduit 120 is corrugated, the corrugation of conduit 120 is preferably designed to have the shallowest valleys possible on the blood-contacting surface consistent with a total wall strain from compression and extension not exceeding 15%. The conduit wall material can, for example, be CORETHANE® polyurethane, which is an implant grade, blood compatible polyurethane.

In one embodiment, a pivot arm 150 captures valve 140 within conduit 120. One end of the pivot arm 150 is attached to pivot point 152 and the other end of the pivot arm 150 captures the valve 140. In the illustrated embodiment, an opening or volume 154 formed in the base of the pivot arm 150 provides space for an eccentric roller bearing 160. The rotation of bearing 160 causes the oscillation of the pivot arm 150 at its valve end and, thereby, oscillation of valve 140.

Figure 3A:
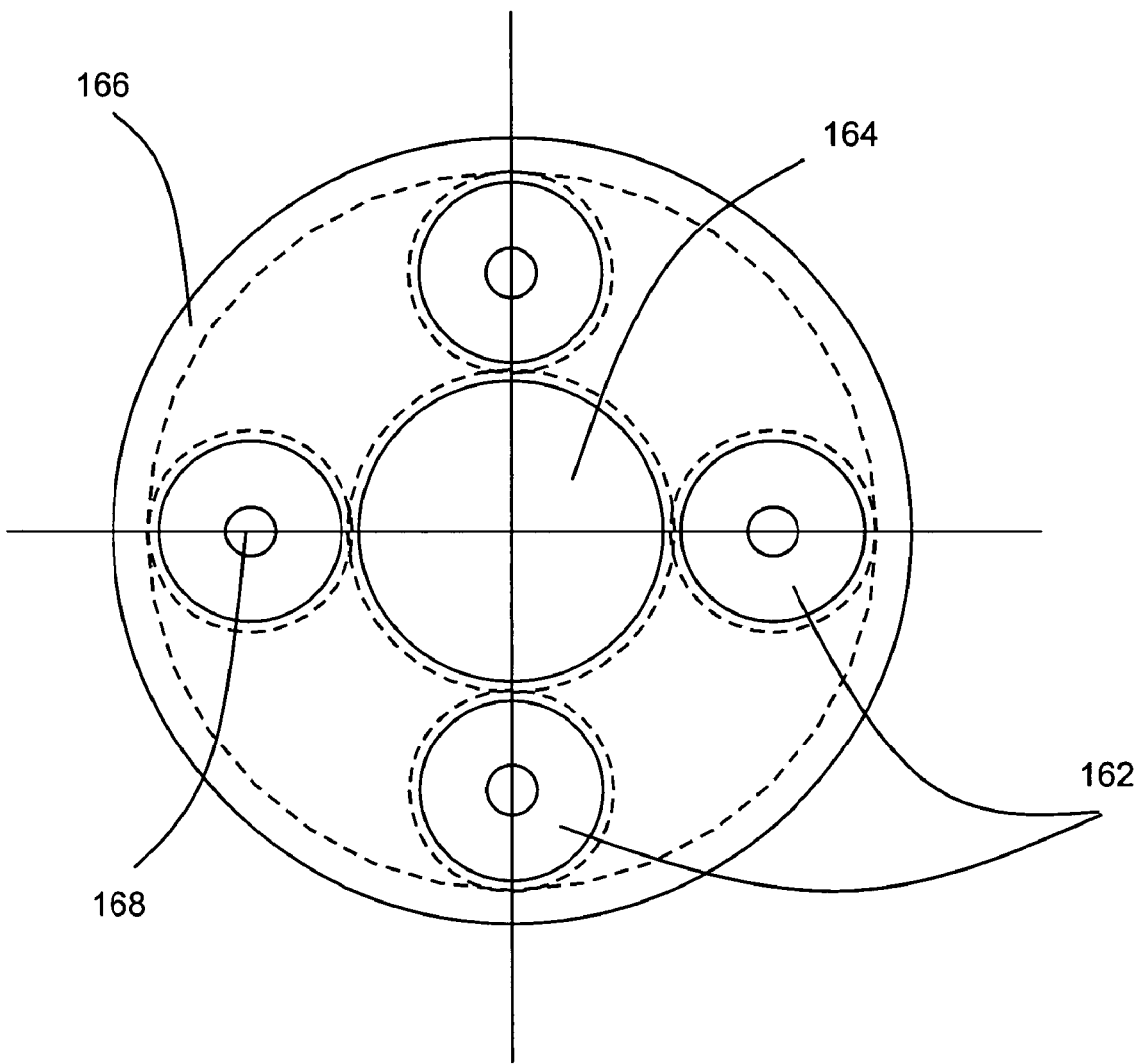
FIG. 3A is a side view of a planetary gear arrangement that reduces the speed of the rotating motor in FIG. 3 and includes rotating planet gears that can be connected to a carriage which rotates the eccentric bearing of FIG. 3 to drive the pivot arm and oscillate the valve.

A gear system including, for example, one or two sets of planetary gears can be used to reduce motor rotation speed. For example, FIG. 3A illustrates an embodiment of a set of planetary gears 162 that reduces the motor's rotational speed to the rotational speed needed to rotate the eccentric bearing 160 which oscillates the pivot arm 150. A sun gear 164 is driven by the motor rotor and, in turn, drives each of the four planet gears 162 as they travel around and are captured by the stationary ring gear 166. A carriage 169 (see FIG. 4) connects to the four axels 168 of the planet gears 162 and drives the eccentric bearing 160.

If there are two planet gear sets, they can be arranged on both sides of the motor for balance. An eccentric roller bearing connected to one or both the planet gear carriages can induce the needed oscillatory motion in one or both the pivot arms. The shape of the cut out section in the pivot arms that contact the roller bearings will determine the specifics of the oscillatory motion.

To be implantable, the motor, gears, bearings and pivot arms of the present invention are preferably resistant to the corrosive environment of the body. The motor stator and rotor can, for example, be encased in a hermetically sealed corrosion resistant titanium case. The gears can, for example, be constructed of a corrosion resistant engineering plastic such as polyetheretherketone (PEEK). The eccentric bearing can, for example, be constructed of corrosion resistant ceramic rolling elements and races.

As valve 140 moves forward, it's valve ports close and valve 140 drives blood forward toward the outflow graft 107. The motion of valve 140 is then reversed and it's valve ports open during repositioning of valve 140 for the next forward motion. The distance traveled in any one direction can, for example, be 1 to 2 centimeters. The cross sectional area of the valve 140 can, for example, be 5 square centimeters. As one example, the valve stroke of such a valve can be 1.6 centimeters, resulting in a displaced volume of 8 milliliters. It has been found by experimentation that at cycle rates between, for example, 8 and 20 cycles per second, an aqueous fluid will flow continuously forward because of a momentum effect even though roughly half the time the valve 140 is moving backwards. For example, three cycles of 1.6 centimeter valve movement of the above-described valve displaces roughly 3 times 8 or 24 milliliters of blood and the actual flow in the forward direction could be the same or even greater than this amount. If this pumping routine occurred late in the ventricular contraction period (that is, in the later half of systole) when a failing left ventricle is too weak to eject blood by itself, an incremental output of about 24 milliliters or greater can be realized. This output would be enough extra flow to compensate for the low cardiac output found in typical heart failure.

A very space and energy efficient drive mechanism for the rotating bearing 160 is a brush-less direct current or DC motor 170 that is connected to one or more sets of planetary gears as described above. In one embodiment, motor 170 includes a stationary stator 172 and a rotor 174 positioned within a space or chamber 134 within housing 130. A planetary gear speed reduction of 3 to 1 would, for example, translate a motor rotation speed of 3,000 revolutions per minute to three revolutions of the bearing 160 in 180 milliseconds. In this example, the motor 170 can be started prior to the desired assist period and reach a speed of 3,000 RPM, The motor 170 can be stopped after the desired number of assist cycles. Once again, to balance forces, two sets of planetary gears, eccentric bearings and pivot arms can be placed on opposite sides of the motor and the pump, each driven by the respective ends of the motor rotors axel.

Figure 4:
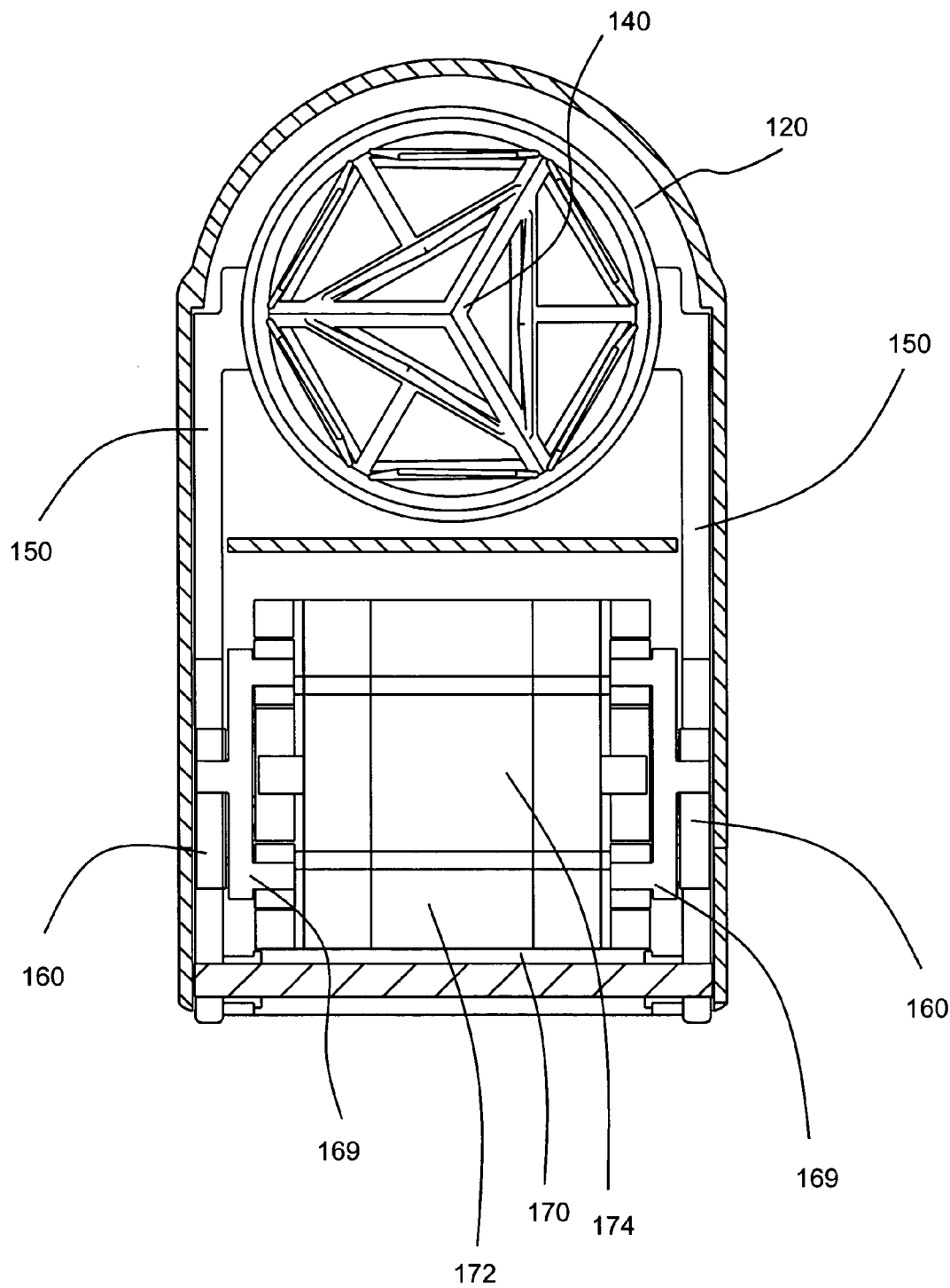
FIG. 4 is a mid-cross sectional view of the pump shown in FIG. 3.

FIG. 4 is a mid-cross sectional view of pump 100. Valve 140, is driven by pivot arm 150 as described above. The motor stator 172 induces rotation in rotor 174, which, in turn, rotates the eccentric bearing 160 through the planetary gears 162.

Design work and bench testing have demonstrated that it is possible to pump a sufficient volume of fluid (namely water, which for the test purposes was equivalent to blood) by oscillating single valve 140 within moveable conduit 120 without an associated pipe or tube. Elimination of such a pipe or tube is facilitated, for example, by use of a mechanical connection between the moving valve and the drive mechanism such as an extending arm (for example, pivot arm 150) which mechanically connects valve 140 to a drive mechanism such as motor 170. In that regard, in a number of previously described moving valve pumps, it is necessary to place drive elements such as magnets on a linear pipe or tube in which the moving valve is placed. Valve 140 moves (oscillates) in an arcuate path as a result of its connection to pivot arm 150. Although a single moveable valve can provide sufficient flow, more than one moveable valve can be used in the pumps of the present invention. In the case that two valves are used, the motion of the valves can be out of phase by 180 degrees so that one valve is moving forward while the other valve is moving rearward.

Figure 5:
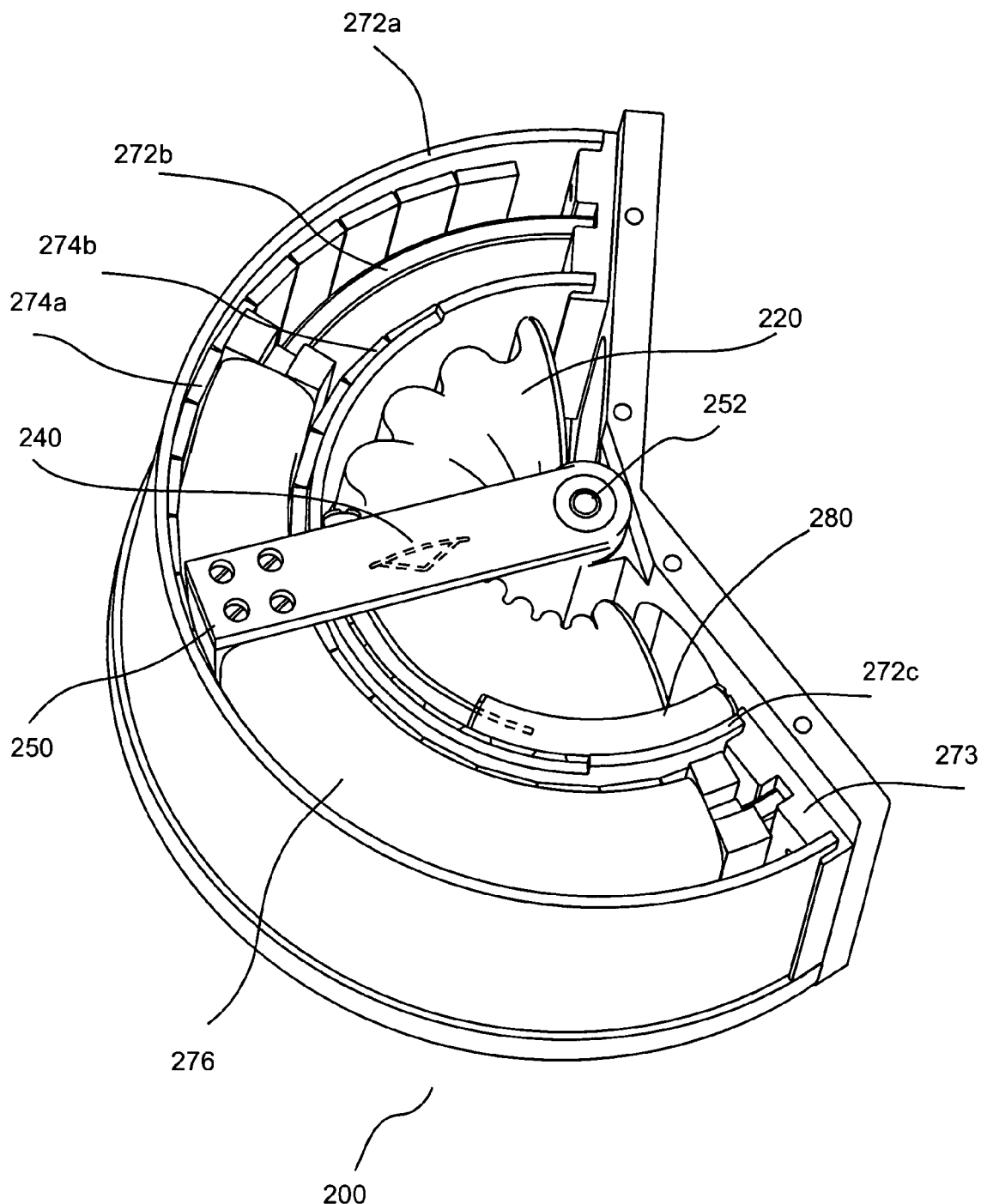
FIG. 5 is a perspective view of another embodiment of a pump of the present invention including a direct electric motor drive mechanism.

As described above, the actuating pivot arm 150 connects the valve 140 to a drive mechanism, which in the embodiment of FIGS. 3 through 4 is the brushless, direct current electric motor 170 that is speed reduced by a gear mechanism. Other drive mechanisms can be used to oscillate the valves of the present invention. For example, an electromagnetic motor without gears can be used to directly actuate a pivot arm. In that regard, FIG. 5 illustrates an embodiment of a pump 200 of the present invention in which a blood conduit 220 is positioned between a direct drive electric motor 270 and a pivot point 252 of a pivot arm 250. The stretchable corrugated blood flow conduit 220 is formed in a curvilinear fashion and has a single one-way valve 240 placed generally in the mid-position of conduit 220. The valve 240 is attached to pivot arm 250, which is made to oscillate with an arcuate motion driving the valve 240 forwards and backwards in the blood flow pathway 220. When driving forwards, valve 240 is closed and accelerates the blood into the patient's circulation. When driven backwards, the valve ports of valve 240 open, allowing the momentum of the blood to continue forward blood flow. This oscillating valve movement occurs for one to several or more cycles (for example, from 1 to 10 cycles of from approximately 1 to 20 millimeters, and preferably 5-20 millimeters, in length) during each natural heart beat, depending on the degree of intended assist for the failing left ventricle.

The pivot arm 250 operatively connects the valve 240 to the motor 270, which powers the oscillating pivot arm motion. In the illustrated embodiment, motor 270 includes three curved or arcuate magnetically conductive plates 272a, 272b and 272c. The magnetically conductive material of plates 272a, 272b and 272c can, for example, be a high-ferrous content steel suitably coated to protect against corrosion. The plate ends are magnetically connected with end plates 273, which can be made from the same material as the plates 272a, 272b and 272c and placed to establish the magnetic circuit. Permanent magnets 274a and 274b made from, for example, neodymium-iron-borate are placed on the surfaces of plates 272a and 272c that face plate 272b. The magnetic flux lines on each side of plate 272b are of opposite polarity, with north to south in one gap and south to north in the other gap. Curved coil 276 wraps around plate 272b. The electrically conductive wire of coil 276 can, for example, be made from copper or aluminum, which is preferably suitably coated to prevent corrosion. Unlike other moving valve pumps, the present inventors have found that a lighter weight of the coil 276 (as compared to a moving magnet or magnets) allows acceleration and deceleration with less force and provides more efficient operation. In this regard, using aluminum wire provides a better mass to conductivity ratio than copper. In that regard, aluminum has approximately one-third the mass and two-thirds the conductivity of copper. Thus, for purposes of minimizing the acceleration and deceleration forces, aluminum is the preferred conductive material. An additional benefit accrues from a leverage advantage wherein the coil 276 moves at approximately twice the speed and half the force as that seen by the valve 240. Passing electric current through coil 276 in one direction causes the coil 276, pivot arm 250 and valve 240 to move in a first angular direction, while passing electric current through the coil 276 in the reverse direction causes the coil 276, pivot arm 250 and valve 240 to move in the opposite angular direction. The size of electric motor 270 is determined by its Km ratio and is more related to motor force than to motor speed.

Regardless of the type of the drive mechanism employed, the position of the valve may be determined at any point in time by, for example, placing a position sensor in operative connection with the pivot arm 250. As illustrated in FIG. 5, a position sensor 280 can, for example, include a curved variable differential transformer, which produces a voltage proportional to the position of the pivot arm 250 and valve 240. The transformer 280 can be curved in shape to accommodate the curved motion of the pivot arm 250 and the connected valve 240. The derivative of this position signal with respect to time is the velocity and the second derivative is the acceleration. Using this information, a microprocessor and motor controller (not shown in FIG. 5) can induce virtually any desired motion profile.

In the embodiment of a gearless electromagnetic motor drive discussed above, the valve 240 is placed at an intermediate position on the pivot arm 250, between the pivot point 252 and the moving coil 276 of the motor 270. As clear to one skilled in the art, however, in the case of an electromagnetic motor, either the magnet or the coil can be move and the opposite element held stationary. As with motor 170, any corrodible elements of the motor 270 are preferably appropriately fabricated or coated to prevent corrosion.

In general, it is easier to manufacture a small pump using a gear-speed-reduced motor drive mechanism as described in connection with FIGS. 3 through 4 than using a gearless electromagnetic motor as described in connection with FIGS. 5 and 6. In the case of a gearless electromagnetic drive mechanism as described in connection with FIGS. 5 and 6, however, compactness can be accomplished by forming the cross sectional area of the electric coils 276, the blood flow conduit 220 and the valve 240 in the form of a racetrack (that is, in the form of an oval or a rectangle with rounded corners). Such a racetrack form is wider than it is high, making the pump 200 somewhat wider but have less stacked height. The height of the pump is the dimension most likely to interfere with the limited dimensions of the chest cavity.

Motion of the valve 240 induced by the ejection of the blood from the left ventricle can also be sensed via, for example, sensor 280 (as described above) in operative connection with pivot arm 250 and, thereby, with valve 240. Sensor 280 is placed in communicative connection with the microprocessor/controller. The sensed valve motion can, for example, be used to detect ventricular contraction, which is the time during which the left ventricle is attempting to eject blood. Once again, the preferred time for valve oscillation assist is later in the contraction period or systole when the ventricle is contracting but doing little flow work. At this time the valve 240 can more easily move blood from the ventricle because the pressure in the ventricle is high and the valve 240 simply needs to add a little more pressure to move the blood. Preferably, valve 240 is oscillated only in the later half of systole.

Figure 6:
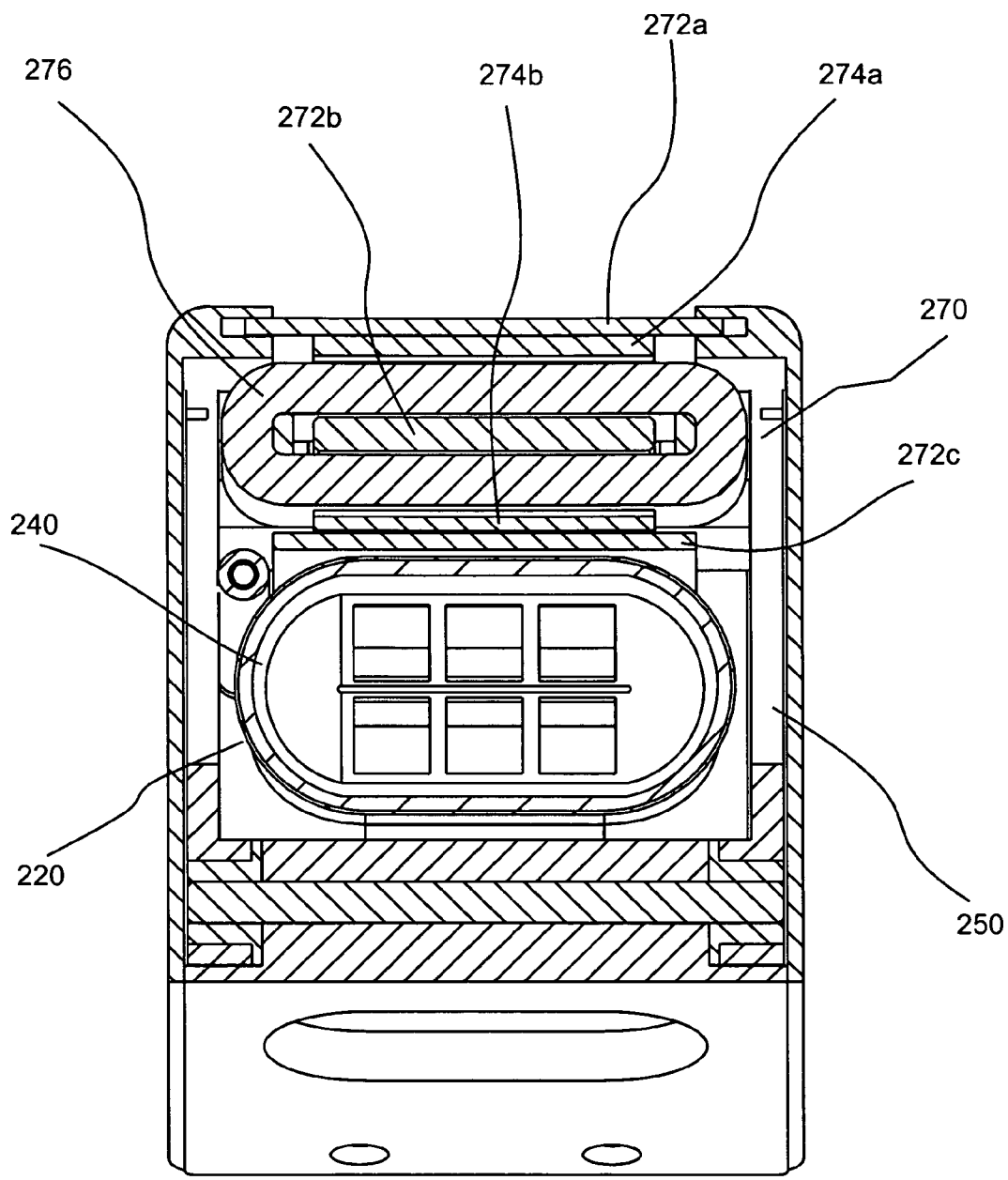
FIG. 6 is a mid-cross sectional view of the pump shown in FIG. 5.

FIG. 6 illustrates a mid-cross sectional view of the direct electric motor drive pump 200. The coil 276 wraps around the intermediate steel plate 272*b*. Plates 272*a* and 272*c*, in connection with attached magnets 274*a* and 274*b*, create the magnetic flux that drives the coil 276 in one or the other direction depending on the direction of current in the coil. Once again, to establish a compact form factor, the electric coils 276, the blood flow conduit 220 and the valve 240 are in the form of a race tract.

FIGS. 6A and 6B illustrate another embodiment of a pump 300 including two moveable valves 340*a* and 340*b* positioned within a generally linear flexible conduit 320 having an inlet 322 and an outlet 324 which can be placed in fluid connection with a blood vessel as described above. The pump 300 includes an electromagnetic motor 370 including moving coils 376*a* and 376*b*, an annular magnet 374, and a ferromagnetic stator 372. Coils 376*a* and 376*b* move up and down (in the orientation of FIGS. 6A and 6B) depending upon the polarity of the voltage applied to the coils 376*a* and 376*b* and the moving coils 376*a* and 376*b* are connected to the valves 340*a* and 340*b* by extending or connection members 350*a* and 350*b*, respectively. As illustrated in FIG. 6A, the magnet 374 is interrupted to make space for a position sensor such as a linear variable differential transformer 380, or LVDT, which provides coil position information for the valve actuator position to a control system 390 (shown schematically in FIG. 6A) of pump 300.

The two valve actuators of pump 300 are provided in series whereby the pump's control system forces the respective motions of the coils 376*a* and 376*b* to be equal and opposite, resulting in the motion of valve 340*a* being 180° out of phase with the motion of valve 340*b*. Such out of phase motion can, for example, operate to reduce any vibratory effects that can occur with a single valve actuator. Patient perception of pump operation can thereby be eliminated or substantially reduced. Moreover, pump 300 can operate as a positive displacement pump because one or the other valves 340*a* and 340*b* is always virtually closed moving forward when the pump 300 is operating. Position sensor 380 can be used in effecting such control.

Another drive mechanism that can be used in connection with the pumps of the present invention is based on pressurized hydraulic fluid. For example, an electric motor may drive an internal gear or gerotor hydraulic pump producing fluid at a pressure approximately ten times that of aortic blood pressure. This relatively high pressure enables driving of an actuator such as a vane, which is in operative connection with a pressurizing or moving valve, to be accomplished with only a few milliliters of fluid. The fluid can, for example, be switched to one or the other side of a vane, piston or piston equivalent. The switching produces an oscillatory movement of the piston, which in turn is connected to the actuating pivot arm moving valve combination.

Figure 7:
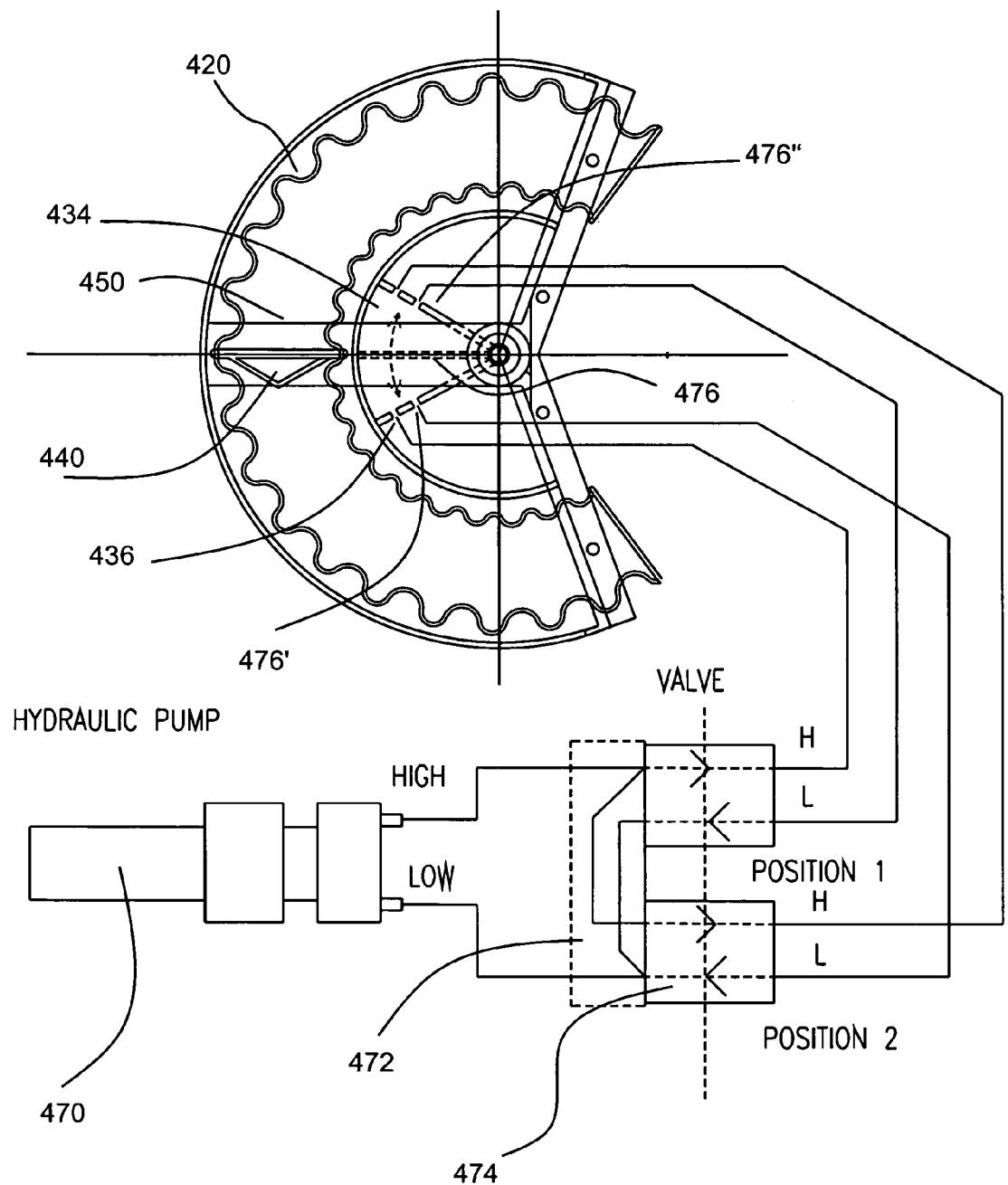
FIG. 7 is a view of another embodiment of a pump of the present invention including a hydraulic drive mechanism.

FIG. 7 illustrates a representative embodiment of a pump 400 of the present invention in which a hydraulic pump 470 develops pressurized fluid at a high-pressure output port. Fluid is returned to hydraulic pump 470 via a low-pressure return port. The fluid lines from the hydraulic pump 470 are connected to manifold 472, which is attached to a four-way, two-position spool valve 474. The valve 474 is electrically activated to one of two positions. In the first position, the spool valve 474 introduces high-pressure fluid into a fluid chamber 434 at port 436. A vane 476 moves in response to the high-pressure fluid and moves the pivot arm 450 and its connected pressurizing valve 440 within the blood conduit 420. With spool valve 474 in the second position, high-pressure fluid is introduced into chamber 434 on the opposite side of vane 476 causing vane 476 to move within a chamber defined by walls 476' and 476", thereby effecting repositioning of the pivot arm 450 and the attached valve 440. In the case of a hydraulic drive mechanism, the hydraulic pumping source can be separate from the blood pump, thereby allowing the blood pump to fit more easily in the upper right chest of the patient.

For each of the drive mechanisms described above, the blood-moving or pressurizing valve preferably requires little reverse blood flow to close the valve. Excessive back flow during valve closure steals from the volumetric efficiency of the pump. Unless valve 140 and other pressuring valves of the present invention are volumetrically efficient in their opening and closing actions, substantial inefficient valve closing backflow will occur as the valve opens and closes several times within a single ventricular contraction time period. As illustrated, for example, in FIGS. 8 through 9, valve 140 can include a plurality of ports 142 formed in a frame 146. Each port 142 has a closing mechanism or valve such as a leaflet or a membrane 144 in operative connection therewith. The leaflets or membranes 144 collectively open and close the valve 140. Using a plurality of relatively small valve ports 142 minimizes the relative amount of reverse blood flow needed to close the valve 140.

Figure 8:
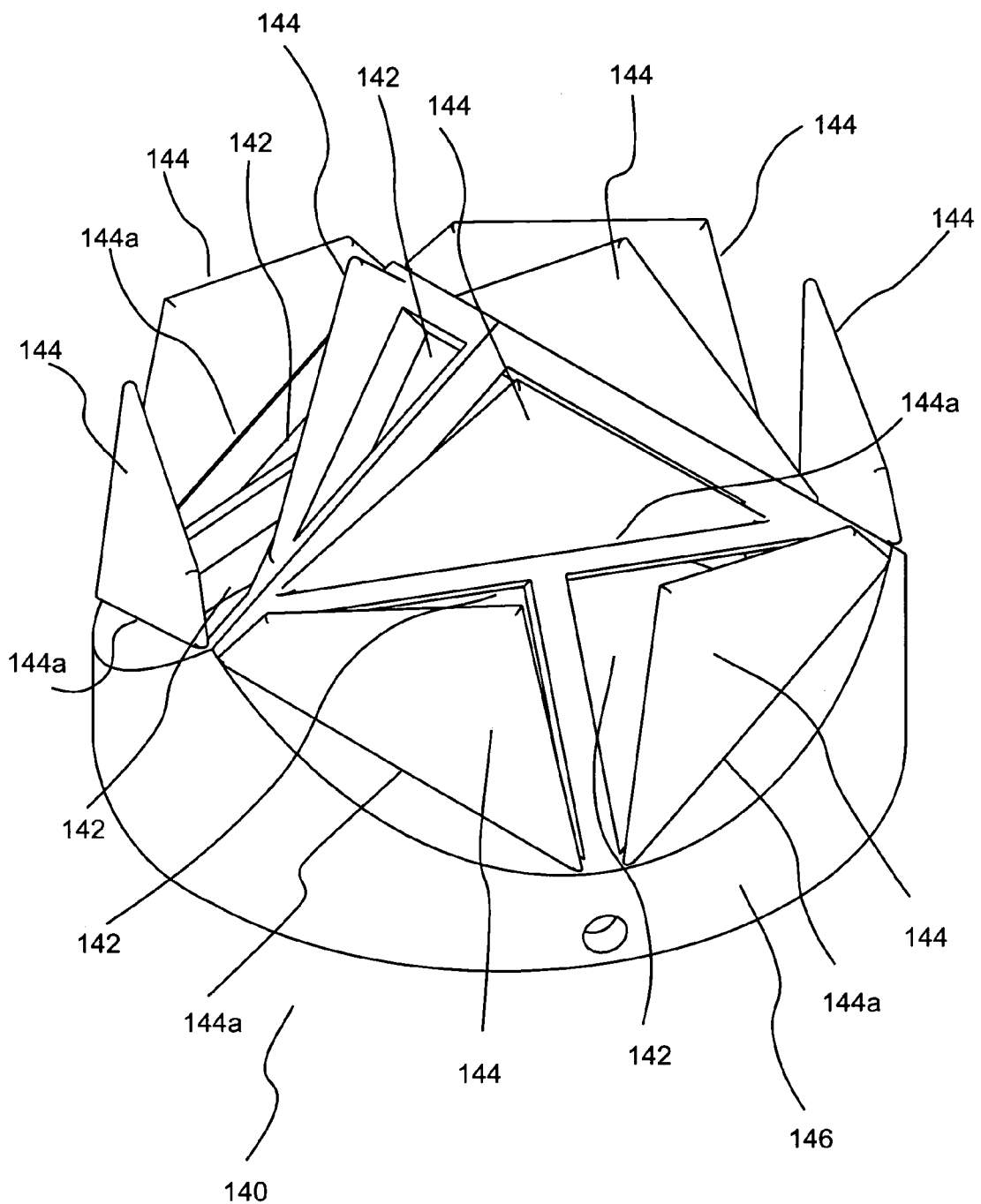
FIG. 8 is a perspective view of an embodiment of a low regurgitant valve suitable for use in the pumps of the present invention wherein the valve ports are in an open position.

For valve longevity purposes it is desirable to minimize the strain experienced by the valve leaflets 144. The valve leaflets or membranes 144 can, for example, be made from polyurethane with a thickness of approximately 10 mils. Strain minimization can, for example, be accomplished by having the leaflets or membranes 144 (as shown in FIGS. 8 through 9) hinge without complex curvature or wrinkling. In general, complex curvature refers to a change in the direction of curvature over the surface of the leaflet or membrane as, for example, occurs in a crinkle which curves in more than two dimension as opposed to a simple curve which occurs in two dimensions. Overstressing of membranes 144 can lead to material fatigue and valve membrane fracture. In the embodiment of FIGS. 8 through 9, each of the plurality of membranes 144 is attached to valve frame 146 along a generally linear path to create a linear hinge 144*a*. As the valve 140 is retracting, the membranes 144 open up to pass blood though the valve 140. When the valve 140 reverses to move forward, the membranes 144 close with very little backward blood flow. As illustrated, for example, in FIGS. 8 through 9, the valve frame 146, valve ports 142 and membranes 144 are preferably angled tilted at an angle θ (see FIG. 8B) of, for example, an angle of 30 to 45 degrees with respect to a radially oriented plane bisecting conduit 120 (or with respect to the general direction of blood flow through conduit 120 as represented by the arrow in FIG. 8B) to minimize blood-closing volume. With the support of the valve membrane frame 146 or seating structure, the membranes 144 push the blood in a forward direction upon forward motion of valve 140.

Figure 8B:
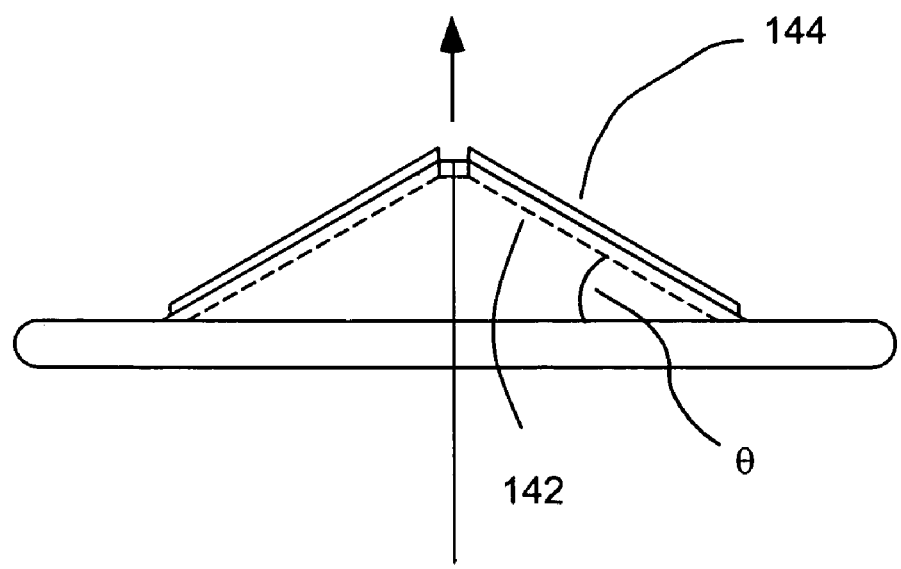
FIG. 8B is a side view of valve ports of the valve shown in FIG. 8 with the attached flexible membrane in a closed state.
Figure 8A:
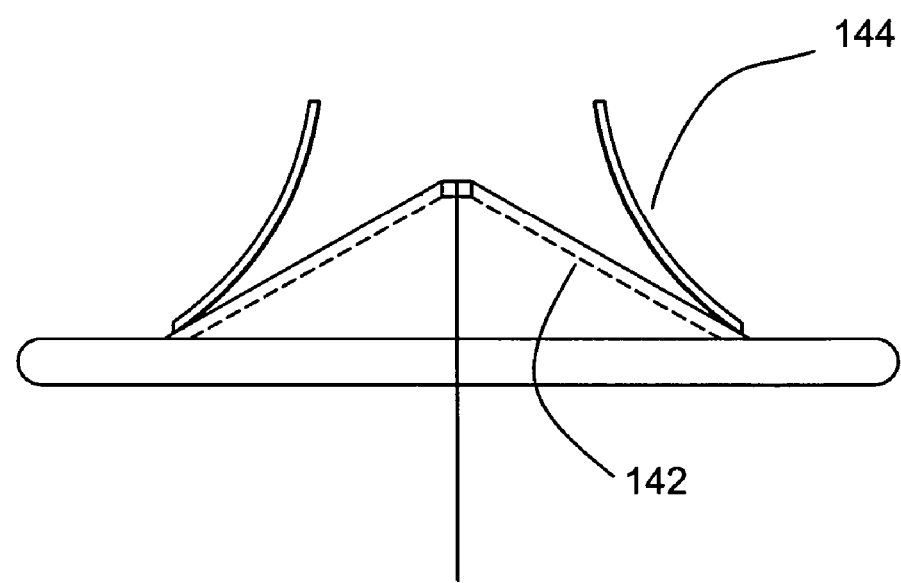
FIG. 8A is a side view of valve ports of the valve shown in FIG. 8 with the attached flexible membrane in an open state.
Figure 9:
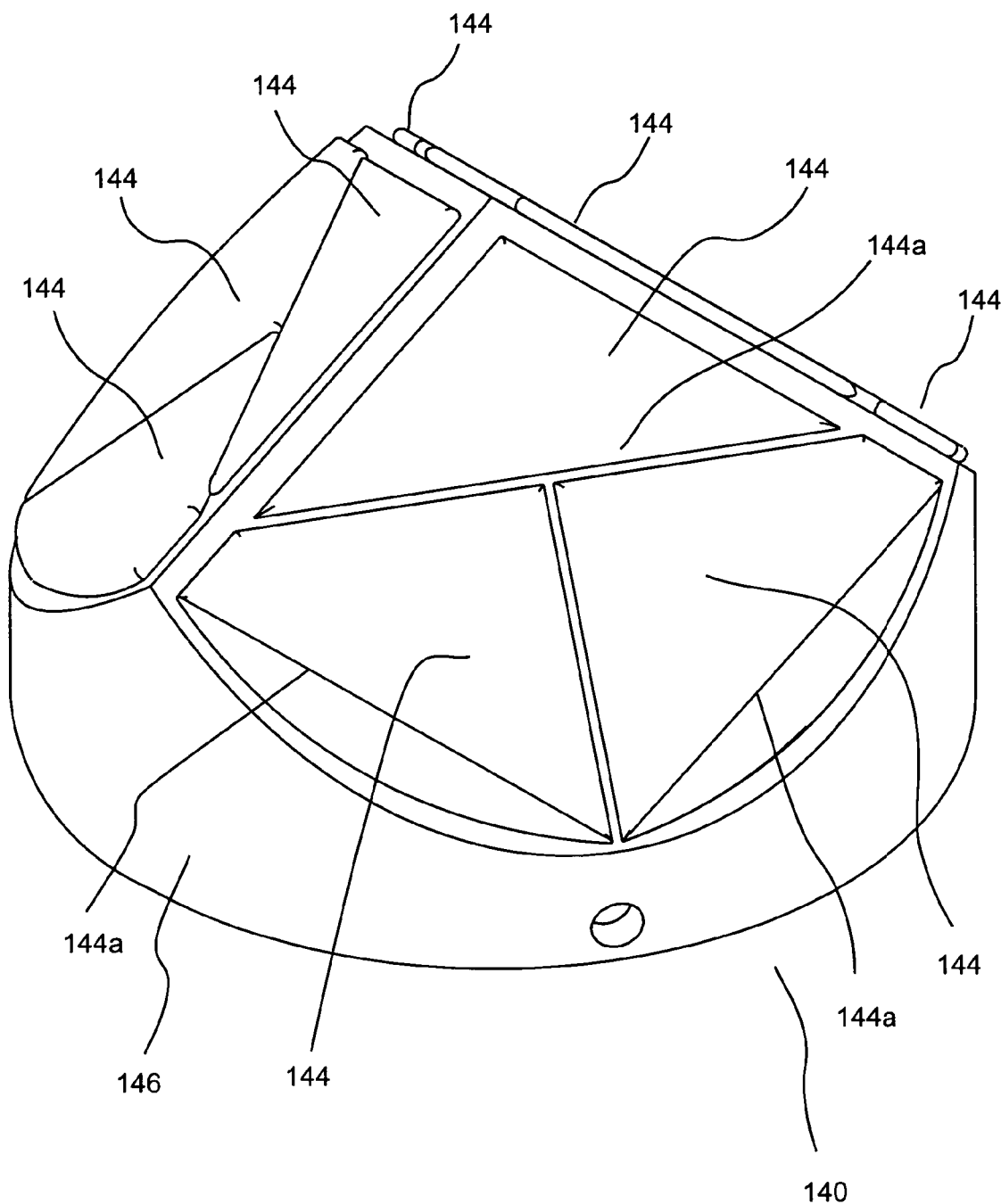
FIG. 9 is a perspective view of the valve shown in FIG. 8, wherein the valve ports are in the closed position.

FIGS. 8A and 8B show a side view of a valve port 142 with the flexible membrane 144 attached at the bottom edge of the port 142. As the valve port 142 opens, membrane 144 gradually curves upward (see FIG. 8A) to allow blood to flow through the port. It has been demonstrated in bench testing that the membranes 144 gradually distribute bending over much of the membranes length to minimize strain.

Figure 10:
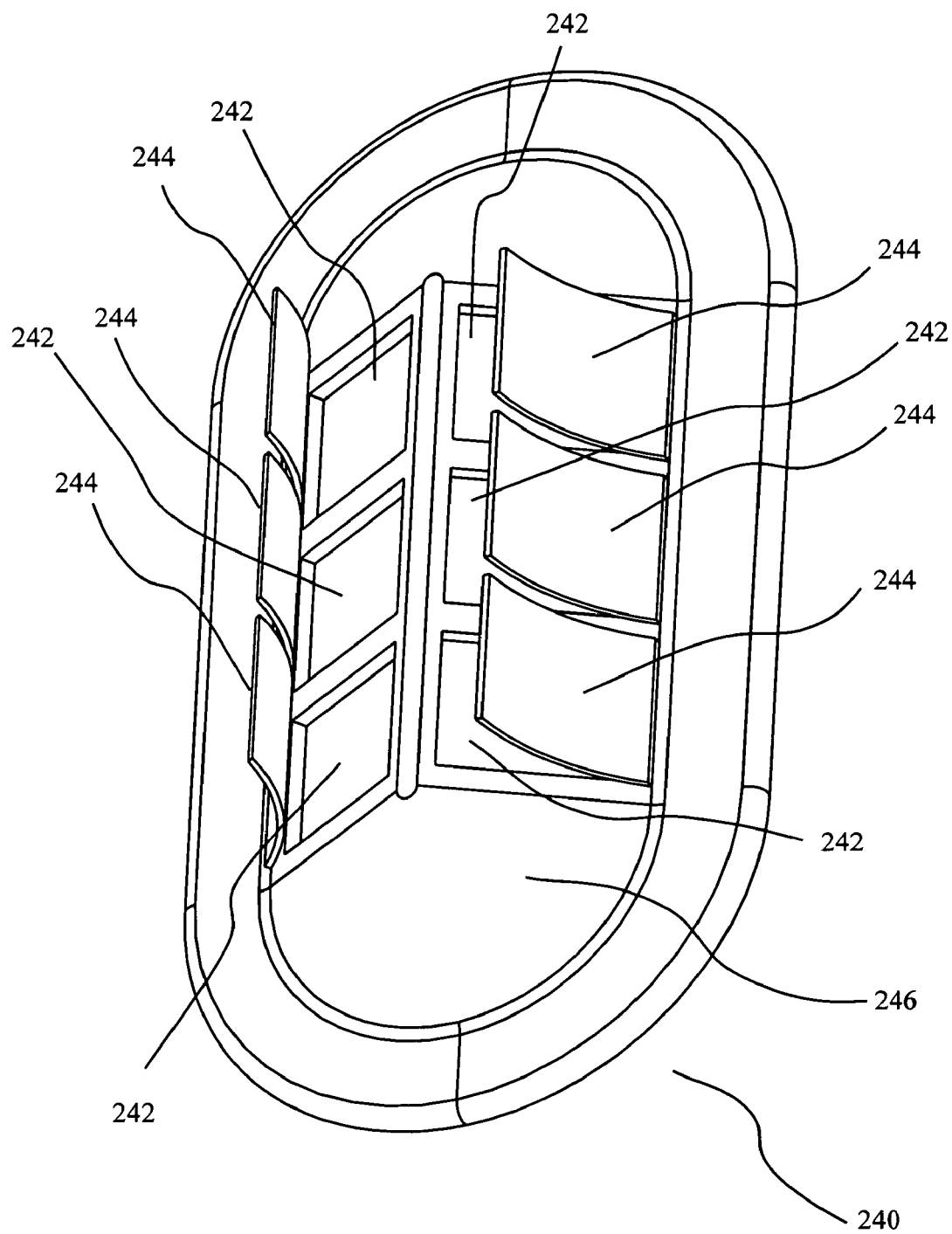
FIG. 10 is a perspective view of another embodiment of a valve suitably shaped for use in the pump shown in FIG. 5.

As illustrated in FIG. 10 valve 240, having a racetrack shape for use with pump 200, also includes a plurality of ports 242 formed in a frame 246. Likewise, each of valve ports 244 has a flexible leaflet or membrane 246 in operative connection therewith via a generally linear hinging attachment 246a.

The valves of the present invention provide for substantially failsafe operation of the pumps of the present invention. In that regard, if power to the pump fails or the pump otherwise malfunctions, the patient is no worse off than if the pump were not in place. As the valve ports require only a few millimeters of mercury or less increased pressure to pump blood through the valve ports, blood is free to flow through the flow conduits of the pumps of the present invention even if the pump is inoperable.

When the pumps of the present invention are connected in series with the ascending aorta, a small amount of leakage through the blood-moving valve can be provided to allow reverse blood flow during the heart's resting period or diastole. This reverse flow will supply blood to the coronary arteries and the heart itself. This leakage can be produced by purposeful misalignment of one or more of the leaflets and sealing structure/frame (to effect incomplete closure of the corresponding valve openings) or by having a permanent hole in the valve structure. Approximately 500 milliliters per minute of blood leakage is required for coronary flow.

As described above, the corrugated blood conduit 120 and the valve leaflets or membranes 144 can be constructed of polyurethane having a wall thickness of approximately 10 mils. Bench testing has demonstrated flexing life well in excess of 200 million cycles as long as the induced combined strains in the polyurethane do not exceed 15%.

As also described above, if the corrugation valleys in conduit 120 are too deep, there is a risk of blood stagnation and clotting in the valleys of the corrugation 120. The optimum corrugation design keeps the strain below 15% and minimizes the depth of the corrugation valleys. This optimization can be facilitated by having the pressure outside the conduit 120 approximately equal to the pressure inside the conduit 120 and thereby eliminating pressure induced strain in the conduit 120. If the enclosure formed by housing 130 and header 132 of the assist device or pump 100 seals in a fluid tight fashion and encloses a certain volume of fluid 138 (see FIG. 3) as readily determined by one skilled in the art for a particular pump geometry, the pressure on both sides of the conduit wall will be automatically equalized. Additionally or alternatively, generally rigid elements 122 (see FIG. 3) can be placed around the circumference of conduit 120 at various positions thereon to assist in maintaining the shape thereof. One or more of such elements can be attached to and supported by housing 130.

Depending on the particular drive method used, the control system for the pump can vary. A control system for use in connection with blood pumps is described, for example, in U.S. Pat. No. 6,375,607 by Prem, the disclosure of which is incorporated herein by reference. In FIG. 1, a control system 180 in operative connection with motor 170 of pump 100 is represented schematically. As illustrated in FIG. 1, the control system 180 can, for example, be implanted subcutaneously at a position remote from pump 100 in the upper chest of the patient and placed in communicative connection with pump 100 (for example, via wiring). The control system for valve movement of the pumps of the present invention can, for example, include a microprocessor based position servo control system. A command position signal can, for example, be compared with the actual position signal and an error signal can be generated to cause the motor to speed up or slow down depending on the sign of the error signal. The velocity, acceleration and jerk of the valve movement can all be derived from the position signal changes over time. With the motor turned off, a measure of the blood flow rate through the valve can be obtained by measuring the valve movement as blood is sweeping through the valve. Alternatively, if the valve is held in a fixed position or allowed to move slowly by the servo system, the electrical current required to resist valve movement from the blood flow can be used as a surrogate signal for blood flow rate coming from the left ventricle. The higher the blood flow rate, the more current it takes to hold a fixed valve position or to move the valve against the blood flow. This information can be used to determine the timing of ventricular systole and the timing for valve oscillation. Alternatively, an electrocardiogram can be used to time the valve oscillations. In FIG. 1, leads 182a and 182b provide a signal of the heart's rhythm to control system 180. As described above, the most advantageous time to oscillate the valve is later in systole when the heart is pumping little blood but is generating pressure that the valve can use in its forward stroke.

FIG. 11 illustrates the temporal relationship between several system variables during pump assist. In FIG. 11, the moving valve position, the aortic root blood flow, the contracting left ventricle (18a and 18b), and the electro-cardiographic signal are all juxtaposed along a horizontal time line. One ventricular contraction 18b, is shown without pump assist. A second ventricular contraction 18a, is shown with pump assist. In connection with the FIG. 11, for a representative example of a normal sized male with a heart rate of 80 beats per minute, the volume of blood ejected from the failing left ventricle increases from approximately 37 milliliters to a normal level of 52 milliliters with the assist action of three cycles of the moving valve pump. Left ventricular contraction wall motion increases with assist (illustrated by the arrows drawn in connection with the left ventricle (18a and 18b) in FIG. 11) as more blood leaves the ventricle with the decreased after-load resulting from the pumping action of the moving valve.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. An implantable pump for assisting blood flow, comprising:
    a flexible conduit;
    at least one valve attached to the flexible conduit about the perimeter of the valve; and
    a drive mechanism to move the valve to pump blood within the conduit,
    wherein the flexible conduit is arced and the drive mechanism is adapted to oscillate the valve on an arced path.

2. The pump of claim 1 wherein valve is in operative connection with a pivot arm which is in operative connection with the drive mechanism.

3. The pump of claim 2 wherein the drive mechanism comprises a brushless direct current electric motor.

4. The pump of claim 3 wherein the drive mechanism further comprises a speed reduction mechanism in operative connection with the brushless direct current motor and the valve.

5. The pump of claim 4 wherein the speed reduction mechanism comprises a gear system.

6. The pump of claim 2 wherein the drive mechanism comprises an electromagnetic motor comprising at least one curved magnetically conductive plate.

7. The pump of claim 6 wherein the electromagnetic motor further comprises at least one movable coil.

8. The pump of claim 7 wherein the at least one moveable coil comprises aluminum wiring.

9. The pump of claim 2 wherein the drive mechanism comprises at least one hydraulic pump.

10. An implantable pump for assisting blood flow, comprising:
    a flexible conduit;
    at least one valve attached to the flexible conduit about the perimeter of the valve,
    wherein the valve comprises a plurality of openings, each of the plurality of openings having a closure mechanism in operative connection therewith, each closure mechanism being operable to at least partially close the opening to which it is operatively connected when the moveable valve is moved forward and to open the opening to which it is operatively connected when the valve is moved rearward; and
    a drive mechanism to move the valve to pump blood within the conduit.

11. The pump of claim 10 wherein each of the closure mechanisms comprises a flap of resilient material.

12. The pump of claim 11 wherein flexing of each of the flaps is distributed over a length of the flap.

13. The pump of claim 11 further comprising an inflow conduit in fluid connection with a first, inflow end of the flexible conduit, an outflow conduit in operative connection with a second, outflow end of the flexible conduit, and a generally cylindrical flow device that is insertable within a blood vessel, the flow device comprising a first flow path in fluid connection with an inlet of the flow device and a second flow path in fluid connection with an outlet of the flow device, the first flow path and the second flow path crossing within the flow device, the inflow conduit being in fluid connection with the first flow path and the outflow conduit being in fluid connection with the second flow path.

14. The pump of claim 11 further comprising a control mechanism in operative connection with the drive mechanism.

15. The pump of claim 14 wherein the control mechanism is adapted to actuate the drive mechanism only during the later half of systole.

16. The pump of claim 14 wherein a signal of the heart's rhythm is provided to the control mechanism to time valve movement so that the drive mechanism moves the valve to pump blood during the later half of systole.

17. The pump of claim 14 wherein a signal of blood flow rate coming from the left ventricle is provided to the control mechanism to time valve movement so that the drive mechanism moves the valve to pump blood during the later half of systole.

18. The pump of claim 14 wherein the control mechanism is adapted to time valve movement so that the drive mechanism moves the valve to pump blood during the later half of systole.

19. The pump of claim 14 wherein the control mechanism is adapted to time valve movement so that the drive mechanism moves the valve to pump blood during the later half of systole.

20. The pump of claim 11 wherein each of the flaps is placed in operative connection with the corresponding opening so that the resilient material of the flap flexes without complex curvature.

21. The pump of claim 11 wherein each of the opening comprises at least one generally linear side and the flap is attached to the generally linear side.

22. The pump of claim 11 wherein each of the openings is angled with respect to the direction of flow.

23. The pump of claim 11 wherein each of the flaps opens to allow blood flow therethrough even if the drive mechanism is not moving the valve.

24. The pump of claim 11 wherein the drive mechanism is adapted to oscillate the valve.

25. The pump of claim 10 wherein each of the openings is angled with respect to the direction of flow.

26. The pump of claim 11 wherein reverse blood flow through the valve occurs during diastole to supply blood to the coronary arteries and heart.

* * * * *

UNITED STATES PATENT AND TRADEMARK OFFICE
CERTIFICATE OF CORRECTION

| | | |
|---|---|---|
| PATENT NO. | : 7,588,530 B2 | Page 1 of 1 |
| APPLICATION NO. | : 11/184231 | |
| DATED | : September 15, 2009 | |
| INVENTOR(S) | : Marlin Stephen Heilman et al. | |

It is certified that error appears in the above-identified patent and that said Letters Patent is hereby corrected as shown below:

Column 18, line 16, claim 18, delete "The pump of claim 14 wherein the control mechanism is adapted to time valve movement so that the drive mechanism moves the valve to pump blood during the later half of systole.";

and insert -- The pump of claim 14 wherein the drive mechanism is adapted to oscillate the valve. --

Signed and Sealed this

Ninth Day of February, 2010

David J. Kappos
*Director of the United States Patent and Trademark Office*